(12) United States Patent
Hall et al.

(10) Patent No.: US 12,102,512 B2
(45) Date of Patent: Oct. 1, 2024

(54) WOUND FILLING APPARATUSES AND METHODS

(71) Applicant: Smith & Nephew PLC, Watford (GB)

(72) Inventors: Kristian David Hall, Hessle (GB); Edward Yerbury Hartwell, Hull (GB); Derek Nicolini, Brough (GB)

(73) Assignee: Smith & Nephew PLC, Watford (GB)

( * ) Notice: Subject to any disclaimer, the term of this patent is extended or adjusted under 35 U.S.C. 154(b) by 415 days.

(21) Appl. No.: 17/673,673

(22) Filed: Feb. 16, 2022

(65) Prior Publication Data

US 2022/0241113 A1 Aug. 4, 2022

Related U.S. Application Data

(60) Continuation of application No. 16/115,064, filed on Aug. 28, 2018, now Pat. No. 11,253,399, which is a
(Continued)

(30) Foreign Application Priority Data

Dec. 6, 2007 (GB) ...................... 0723852
Dec. 6, 2007 (GB) ...................... 0723874
(Continued)

(51) Int. Cl.
*A61F 13/05* (2024.01)
*A61M 1/00* (2006.01)
*A61M 27/00* (2006.01)

(52) U.S. Cl.
CPC .............. *A61F 13/05* (2024.01); *A61M 1/71* (2021.05); *A61M 1/915* (2021.05); *A61M 1/92* (2021.05);
(Continued)

(58) Field of Classification Search
CPC ......... A61F 13/05; A61M 1/71; A61M 1/915; A61M 1/92; A61M 2205/3606; A61M 2205/366
See application file for complete search history.

(56) References Cited

U.S. PATENT DOCUMENTS

| 1,400,124 A | 12/1921 | Wolverton et al. |
| 3,276,472 A | 10/1966 | Jinkens et al. |
(Continued)

FOREIGN PATENT DOCUMENTS

| CA | 1099850 A | 4/1981 |
| CN | 201076519 Y | 6/2008 |
(Continued)

OTHER PUBLICATIONS

Bevan D., et al., "Diverse and potent activities of HGF/SF in skin wound repair," Journal of Pathology, vol. 203, 2004, pp. 831-838.
(Continued)

*Primary Examiner* — Guy K Townsend
(74) *Attorney, Agent, or Firm* — Knobbe, Martens, Olson & Bear, LLP

(57) ABSTRACT

Many embodiments of wound filling devices and methods of their use in systems for the application of negative pressure therapy are described herein. In one embodiment, a wound filling device comprises: an inflatable bag member having at least one fluid carrying conduit operably connected thereto to inflate/deflate said bag member; a separate textured covering sock member at least partially covering the inflatable bag member. Another embodiment comprises a three-dimensional wound packing member, and may optionally comprise a plurality of such members linked together. Certain embodiments of wound packing members may comprise a porous bag member adapted to be non-adherent to the wound. Yet other embodiments may comprise a non-porous
(Continued)

bag member provided with means to connect a fluid supply to the interior.

20 Claims, 11 Drawing Sheets

Related U.S. Application Data continuation of application No. 14/855,214, filed on Sep. 15, 2015, now Pat. No. 10,080,689, which is a division of application No. 13/545,942, filed on Jul. 10, 2012, now abandoned, which is a continuation-in-part of application No. 12/746,504, filed as application No. PCT/GB2008/051114 on Nov. 26, 2008, now abandoned, said application No. 13/545,942 is a continuation-in-part of application No. 12/746,508, filed as application No. PCT/GB2008/051122 on Nov. 26, 2008, now abandoned, said application No. 13/545,942 is a continuation-in-part of application No. 12/746,757, filed as application No. PCT/GB2008/051075 on Nov. 17, 2008, now abandoned, said application No. 13/545,942 is a continuation-in-part of application No. 12/746,753, filed as application No. PCT/GB2008/051134 on Nov. 28, 2008, now abandoned, said application No. 13/545,942 is a continuation-in-part of application No. 12/746,751, filed as application No. PCT/GB2008/051070 on Nov. 17, 2008, now abandoned.

(30) Foreign Application Priority Data

Dec. 8, 2007 (GB) .................................. 0724039
Dec. 8, 2007 (GB) .................................. 0724040
Dec. 8, 2007 (GB) .................................. 0724044

(52) U.S. Cl.
CPC ........... *A61M 2205/3606* (2013.01); *A61M 2205/366* (2013.01)

(56) References Cited

U.S. PATENT DOCUMENTS

| | | |
|---|---|---|
| 3,367,332 A | 2/1968 | Groves |
| 3,750,704 A | 8/1973 | Burke et al. |
| 3,837,922 A | 9/1974 | Ng et al. |
| 4,117,551 A | 9/1978 | Brooks et al. |
| 4,468,219 A | 8/1984 | George et al. |
| 4,538,920 A | 9/1985 | Drake |
| 4,573,965 A * | 3/1986 | Russo .................... A61M 27/00 604/128 |
| 4,664,662 A | 5/1987 | Webster |
| 4,753,536 A | 6/1988 | Spehar et al. |
| 4,759,354 A * | 7/1988 | Quarfoot ................ A61L 15/58 106/154.3 |
| 4,767,026 A | 8/1988 | Keller et al. |
| 4,771,919 A | 9/1988 | Ernst |
| 4,872,450 A | 10/1989 | Austad |
| 4,969,880 A | 11/1990 | Zamierowski |
| 5,010,115 A | 4/1991 | Grisoni |
| 5,064,652 A | 11/1991 | Bay |
| 5,064,653 A | 11/1991 | Sessions et al. |
| 5,073,172 A * | 12/1991 | Fell ....................... A61M 1/732 604/319 |
| 5,080,493 A | 1/1992 | McKown et al. |
| 5,176,663 A | 1/1993 | Svedman et al. |
| 5,207,641 A | 5/1993 | Allton |
| 5,249,709 A | 10/1993 | Duckworth et al. |
| 5,266,326 A | 11/1993 | Barry et al. |
| 5,320,599 A | 6/1994 | Griep et al. |
| 5,333,760 A | 8/1994 | Simmen |
| 5,336,171 A | 8/1994 | Sugarbaker |
| 5,370,610 A | 12/1994 | Reynolds |
| 5,437,651 A | 8/1995 | Todd et al. |
| 5,456,745 A | 10/1995 | Roreger et al. |
| 5,470,625 A | 11/1995 | Perrault |
| 5,549,584 A * | 8/1996 | Gross .................... A61M 1/915 604/319 |
| 5,549,585 A | 8/1996 | Maher et al. |
| 5,582,596 A | 12/1996 | Fukunaga et al. |
| 5,583,114 A | 12/1996 | Barrows et al. |
| 5,609,271 A | 3/1997 | Keller et al. |
| 5,612,050 A | 3/1997 | Rowe et al. |
| 5,630,855 A | 5/1997 | Lundback |
| 5,633,007 A * | 5/1997 | Webb .................... A61F 13/023 602/41 |
| 5,636,643 A * | 6/1997 | Argenta ................ A61F 13/05 602/42 |
| 5,645,081 A * | 7/1997 | Argenta ................ A61M 1/96 602/42 |
| 5,660,823 A | 8/1997 | Chakrabarti et al. |
| 5,717,030 A | 2/1998 | Dunn et al. |
| 5,747,064 A | 5/1998 | Burnett et al. |
| 5,760,754 A | 6/1998 | Amero, Jr. et al. |
| 5,776,193 A | 7/1998 | Kwan et al. |
| 5,786,682 A | 7/1998 | Aiken et al. |
| 5,788,667 A | 8/1998 | Stoller |
| 5,833,642 A | 11/1998 | McCabe et al. |
| 5,834,007 A | 11/1998 | Kubota |
| 5,874,500 A | 2/1999 | Rhee et al. |
| 5,945,115 A | 8/1999 | Dunn et al. |
| 5,962,010 A | 10/1999 | Greff et al. |
| 5,988,842 A | 11/1999 | Johnsen et al. |
| 5,998,472 A | 12/1999 | Berger et al. |
| 6,071,267 A | 6/2000 | Zamierowski |
| 6,129,440 A | 10/2000 | Reynolds |
| 6,135,116 A | 10/2000 | Vogel et al. |
| 6,143,352 A | 11/2000 | Clark et al. |
| 6,165,201 A | 12/2000 | Sawhney et al. |
| 6,168,788 B1 | 1/2001 | Wortham |
| 6,214,332 B1 | 4/2001 | Askill et al. |
| 6,229,286 B1 | 5/2001 | Tokuyama |
| 6,252,129 B1 | 6/2001 | Coffee |
| 6,345,623 B1 | 2/2002 | Heaton et al. |
| 6,391,294 B1 | 5/2002 | Dettmar et al. |
| 6,398,761 B1 | 6/2002 | Bills et al. |
| 6,398,767 B1 * | 6/2002 | Fleischmann ........... A61M 1/92 604/304 |
| 6,447,802 B2 | 9/2002 | Sessions et al. |
| 6,458,109 B1 * | 10/2002 | Henley .................. A61M 1/77 604/289 |
| 6,486,285 B2 | 11/2002 | Fujita |
| 6,495,127 B1 | 12/2002 | Wallace et al. |
| 6,509,031 B1 | 1/2003 | Miller et al. |
| 6,521,251 B2 | 2/2003 | Askill et al. |
| 6,547,467 B2 | 4/2003 | Quintero |
| 6,553,998 B2 | 4/2003 | Heaton et al. |
| 6,575,940 B1 | 6/2003 | Levinson et al. |
| 6,596,704 B1 | 7/2003 | Court et al. |
| 6,627,216 B2 | 9/2003 | Brandt et al. |
| 6,629,774 B1 | 10/2003 | Gruendeman |
| 6,685,681 B2 | 2/2004 | Lockwood et al. |
| 6,692,132 B1 | 2/2004 | Meeker |
| 6,695,823 B1 | 2/2004 | Lina et al. |
| 6,730,299 B1 | 5/2004 | Tayot et al. |
| 6,752,794 B2 | 6/2004 | Lockwood et al. |
| 6,767,334 B1 | 7/2004 | Randolph |
| 6,790,438 B1 | 9/2004 | Constancis et al. |
| 6,814,079 B2 | 11/2004 | Heaton et al. |
| 6,855,135 B2 | 2/2005 | Lockwood et al. |
| 6,903,243 B1 * | 6/2005 | Burton .................. A61F 13/0203 602/56 |
| 6,936,037 B2 | 8/2005 | Bubb et al. |
| 6,951,553 B2 | 10/2005 | Bubb et al. |
| 6,979,324 B2 * | 12/2005 | Bybordi .................. A61M 1/916 604/327 |
| 7,025,742 B2 | 4/2006 | Rubenstein et al. |
| 7,070,584 B2 | 7/2006 | Johnson et al. |

(56) References Cited

U.S. PATENT DOCUMENTS

| | | | |
|---|---|---|---|
| 7,077,832 B2 * | 7/2006 | Fleischmann | A61M 35/00 604/289 |
| 7,108,683 B2 * | 9/2006 | Zamierowski | A61M 1/915 604/304 |
| 7,117,869 B2 | 10/2006 | Heaton et al. | |
| 7,128,735 B2 * | 10/2006 | Weston | A61M 27/00 604/313 |
| 7,129,210 B2 | 10/2006 | Lowinger et al. | |
| 7,195,624 B2 | 3/2007 | Lockwood et al. | |
| 7,214,202 B1 | 5/2007 | Vogel et al. | |
| 7,216,651 B2 | 5/2007 | Argenta et al. | |
| 7,279,612 B1 | 10/2007 | Heaton et al. | |
| 7,303,757 B2 | 12/2007 | Schankereli et al. | |
| 7,381,859 B2 | 6/2008 | Hunt et al. | |
| 7,520,872 B2 * | 4/2009 | Biggie | A61M 1/915 604/319 |
| 7,524,315 B2 * | 4/2009 | Blott | A61M 3/0208 604/317 |
| 7,534,927 B2 | 5/2009 | Lockwood et al. | |
| 7,569,742 B2 | 8/2009 | Haggstrom et al. | |
| 7,615,036 B2 | 11/2009 | Joshi et al. | |
| 7,625,362 B2 | 12/2009 | Boehringer et al. | |
| 7,699,823 B2 | 4/2010 | Haggstrom et al. | |
| 7,700,819 B2 | 4/2010 | Ambrosio et al. | |
| 7,708,724 B2 | 5/2010 | Weston | |
| 7,717,313 B2 | 5/2010 | Criscuolo et al. | |
| 7,722,582 B2 | 5/2010 | Lina et al. | |
| 7,745,681 B1 | 6/2010 | Ferguson | |
| 7,753,894 B2 | 7/2010 | Blott et al. | |
| 7,754,937 B2 | 7/2010 | Boehringer et al. | |
| 7,758,554 B2 | 7/2010 | Lina et al. | |
| 7,759,537 B2 | 7/2010 | Bishop et al. | |
| 7,759,538 B2 | 7/2010 | Fleischmann | |
| 7,759,539 B2 | 7/2010 | Shaw et al. | |
| 7,763,769 B2 | 7/2010 | Johnson et al. | |
| 7,775,998 B2 | 8/2010 | Riesinger | |
| 7,779,625 B2 | 8/2010 | Joshi et al. | |
| 7,790,945 B1 | 9/2010 | Watson, Jr. | |
| 7,790,946 B2 | 9/2010 | Mulligan | |
| 7,803,980 B2 | 9/2010 | Griffiths et al. | |
| 7,811,269 B2 | 10/2010 | Boynton et al. | |
| 7,815,616 B2 | 10/2010 | Boehringer et al. | |
| 7,828,782 B2 | 11/2010 | Suzuki | |
| 7,838,717 B2 | 11/2010 | Haggstrom et al. | |
| 7,846,141 B2 | 12/2010 | Weston | |
| 7,862,831 B2 | 1/2011 | Wang et al. | |
| 7,880,050 B2 | 2/2011 | Robinson et al. | |
| 7,896,823 B2 | 3/2011 | Mangrum et al. | |
| 7,909,805 B2 | 3/2011 | Weston | |
| 7,910,135 B2 | 3/2011 | St. John et al. | |
| 7,922,703 B2 | 4/2011 | Riesinger | |
| 7,964,766 B2 | 6/2011 | Blott et al. | |
| 8,007,164 B2 | 8/2011 | Miyano et al. | |
| 8,012,169 B2 | 9/2011 | Joshi | |
| 8,034,038 B2 * | 10/2011 | Biggie | A61M 1/98 602/42 |
| 8,062,272 B2 | 11/2011 | Weston | |
| 8,062,273 B2 | 11/2011 | Weston | |
| 8,080,702 B2 | 12/2011 | Blott et al. | |
| 8,092,441 B2 | 1/2012 | Sugito | |
| 8,097,272 B2 | 1/2012 | Addison | |
| 8,118,794 B2 | 2/2012 | Weston | |
| 8,119,160 B2 | 2/2012 | Looney et al. | |
| 8,133,211 B2 | 3/2012 | Cavanaugh, II et al. | |
| 8,158,844 B2 | 4/2012 | McNeil | |
| 8,162,907 B2 | 4/2012 | Heagle | |
| 8,192,409 B2 | 6/2012 | Hardman et al. | |
| 8,226,942 B2 | 7/2012 | Charier et al. | |
| 8,241,261 B2 | 8/2012 | Randolph et al. | |
| 8,267,908 B2 | 9/2012 | Coulthard | |
| 8,273,368 B2 | 9/2012 | Ambrosio et al. | |
| 8,282,611 B2 | 10/2012 | Weston | |
| 8,303,552 B2 | 11/2012 | Weston | |
| 8,372,049 B2 | 2/2013 | Jaeb et al. | |
| 8,372,050 B2 | 2/2013 | Jaeb et al. | |
| 8,382,731 B2 | 2/2013 | Johannison | |
| 8,398,614 B2 | 3/2013 | Blott et al. | |
| 8,409,157 B2 | 4/2013 | Haggstrom et al. | |
| 8,410,189 B2 | 4/2013 | Carnahan et al. | |
| 8,460,255 B2 | 6/2013 | Joshi et al. | |
| 8,535,296 B2 | 9/2013 | Blott et al. | |
| 8,545,464 B2 | 10/2013 | Weston | |
| 8,569,566 B2 | 10/2013 | Blott et al. | |
| 8,628,505 B2 | 1/2014 | Weston | |
| 8,753,670 B2 | 6/2014 | Delmotte | |
| 8,795,243 B2 | 8/2014 | Weston | |
| 8,795,247 B2 | 8/2014 | Bennett et al. | |
| 8,795,635 B2 | 8/2014 | Tamarkin et al. | |
| 8,795,713 B2 | 8/2014 | Makower et al. | |
| 8,801,685 B2 * | 8/2014 | Armstrong | A61M 1/912 604/319 |
| 8,834,451 B2 | 9/2014 | Blott et al. | |
| 8,843,327 B2 | 9/2014 | Vernon-Harcourt et al. | |
| 8,961,496 B2 | 2/2015 | Locke et al. | |
| 8,968,773 B2 | 3/2015 | Thomas et al. | |
| 9,028,872 B2 | 5/2015 | Gaserod et al. | |
| 9,205,001 B2 | 12/2015 | Blott et al. | |
| 9,387,126 B2 | 7/2016 | Blott et al. | |
| 9,446,178 B2 | 9/2016 | Blott et al. | |
| 9,452,244 B2 | 9/2016 | Blott et al. | |
| 9,452,248 B2 | 9/2016 | Blott et al. | |
| 9,456,928 B2 | 10/2016 | Haggstrom et al. | |
| 9,526,817 B2 | 12/2016 | Blott et al. | |
| 10,080,689 B2 | 9/2018 | Hall et al. | |
| 2001/0004082 A1 | 6/2001 | Keller et al. | |
| 2001/0029956 A1 * | 10/2001 | Argenta | A61F 13/0246 602/42 |
| 2001/0031943 A1 | 10/2001 | Urie | |
| 2001/0043913 A1 | 11/2001 | Spaans et al. | |
| 2001/0043943 A1 | 11/2001 | Coffey | |
| 2002/0016577 A1 | 2/2002 | Ohmstede | |
| 2002/0019367 A1 | 2/2002 | Vournakis et al. | |
| 2002/0038826 A1 | 4/2002 | Hurray et al. | |
| 2002/0065494 A1 | 5/2002 | Lockwood et al. | |
| 2002/0122771 A1 | 9/2002 | Holland et al. | |
| 2002/0145007 A1 | 10/2002 | Sawhney et al. | |
| 2002/0187182 A1 | 12/2002 | Kramer et al. | |
| 2002/0193721 A1 | 12/2002 | Vandruff | |
| 2002/0198490 A1 | 12/2002 | Wirt et al. | |
| 2002/0198503 A1 | 12/2002 | Risk, Jr. et al. | |
| 2002/0198504 A1 | 12/2002 | Risk, Jr. et al. | |
| 2003/0040478 A1 | 2/2003 | Drucker et al. | |
| 2003/0040687 A1 | 2/2003 | Boynton et al. | |
| 2003/0050594 A1 * | 3/2003 | Zamierowski | A61M 1/915 604/24 |
| 2003/0069535 A1 | 4/2003 | Shalaby | |
| 2003/0097100 A1 | 5/2003 | Watson | |
| 2003/0143189 A1 | 7/2003 | Askill et al. | |
| 2003/0183653 A1 | 10/2003 | Bills | |
| 2003/0208149 A1 | 11/2003 | Coffey | |
| 2003/0212357 A1 * | 11/2003 | Pace | A61M 1/85 602/41 |
| 2003/0212359 A1 | 11/2003 | Butler | |
| 2004/0006319 A1 | 1/2004 | Lina et al. | |
| 2004/0030304 A1 | 2/2004 | Hunt et al. | |
| 2004/0033466 A1 | 2/2004 | Shellard et al. | |
| 2004/0037897 A1 | 2/2004 | Benjamin et al. | |
| 2004/0049187 A1 | 3/2004 | Burnett et al. | |
| 2004/0054338 A1 * | 3/2004 | Bybordi | A61M 27/00 604/313 |
| 2004/0064132 A1 | 4/2004 | Boehringer et al. | |
| 2004/0073152 A1 | 4/2004 | Karason et al. | |
| 2004/0087739 A1 | 5/2004 | Onder | |
| 2004/0167617 A1 | 8/2004 | Voellmicke et al. | |
| 2004/0171998 A1 | 9/2004 | Marasco, Jr. | |
| 2005/0029976 A1 | 2/2005 | Terry et al. | |
| 2005/0065484 A1 * | 3/2005 | Watson, Jr. | A61M 27/00 604/289 |
| 2005/0082435 A1 | 4/2005 | Rasmussen et al. | |
| 2005/0085795 A1 | 4/2005 | Lockwood et al. | |
| 2005/0090787 A1 | 4/2005 | Risk, Jr. et al. | |
| 2005/0131327 A1 | 6/2005 | Lockwood et al. | |

(56) References Cited

U.S. PATENT DOCUMENTS

| | | | |
|---|---|---|---|
| 2005/0137539 A1* | 6/2005 | Biggie | A61M 1/98 604/313 |
| 2005/0148913 A1* | 7/2005 | Weston | A61M 1/964 602/2 |
| 2005/0196450 A1 | 9/2005 | Touitou | |
| 2005/0222544 A1 | 10/2005 | Weston | |
| 2005/0230422 A1 | 10/2005 | Muller et al. | |
| 2005/0244484 A1 | 11/2005 | Flick | |
| 2005/0261642 A1 | 11/2005 | Weston | |
| 2005/0261643 A1* | 11/2005 | Bybordi | A61M 1/916 604/313 |
| 2006/0009744 A1 | 1/2006 | Erdman et al. | |
| 2006/0039742 A1 | 2/2006 | Cable, Jr. et al. | |
| 2006/0079599 A1 | 4/2006 | Arthur | |
| 2006/0100586 A1 | 5/2006 | Karpowicz et al. | |
| 2006/0100594 A1 | 5/2006 | Adams et al. | |
| 2006/0155260 A1* | 7/2006 | Blott | A61M 1/916 604/317 |
| 2006/0173514 A1 | 8/2006 | Biel et al. | |
| 2006/0177490 A1 | 8/2006 | Massouda | |
| 2006/0213527 A1* | 9/2006 | Argenta | A61B 90/00 128/898 |
| 2006/0253082 A1 | 11/2006 | McIntosh et al. | |
| 2006/0273109 A1 | 12/2006 | Keller | |
| 2006/0282028 A1 | 12/2006 | Howard et al. | |
| 2007/0004896 A1 | 1/2007 | Ito et al. | |
| 2007/0009580 A1 | 1/2007 | DiCosmo et al. | |
| 2007/0027414 A1 | 2/2007 | Hoffman et al. | |
| 2007/0032754 A1 | 2/2007 | Walsh | |
| 2007/0032755 A1 | 2/2007 | Walsh | |
| 2007/0032762 A1 | 2/2007 | Vogel | |
| 2007/0032763 A1 | 2/2007 | Vogel | |
| 2007/0032778 A1 | 2/2007 | Heaton et al. | |
| 2007/0055209 A1 | 3/2007 | Patel et al. | |
| 2007/0066945 A1 | 3/2007 | Martin | |
| 2007/0066946 A1 | 3/2007 | Haggstrom et al. | |
| 2007/0118096 A1 | 5/2007 | Smith et al. | |
| 2007/0129707 A1 | 6/2007 | Blott et al. | |
| 2007/0131573 A1 | 6/2007 | Boyles | |
| 2007/0141101 A1 | 6/2007 | Nugent et al. | |
| 2007/0141128 A1 | 6/2007 | Blott et al. | |
| 2007/0147947 A1 | 6/2007 | Stenton et al. | |
| 2007/0156104 A1 | 7/2007 | Lockwood et al. | |
| 2007/0164047 A1 | 7/2007 | Reidt et al. | |
| 2007/0167926 A1 | 7/2007 | Blott et al. | |
| 2007/0167927 A1 | 7/2007 | Hunt et al. | |
| 2007/0185426 A1 | 8/2007 | Ambrosio et al. | |
| 2007/0185463 A1* | 8/2007 | Mulligan | A61M 1/915 424/445 |
| 2007/0203062 A1 | 8/2007 | Ellis-Behnke et al. | |
| 2007/0219512 A1* | 9/2007 | Heaton | A61M 1/96 604/304 |
| 2007/0225663 A1 | 9/2007 | Watt et al. | |
| 2007/0265585 A1 | 11/2007 | Joshi et al. | |
| 2007/0265586 A1 | 11/2007 | Joshi et al. | |
| 2007/0276195 A1 | 11/2007 | Xu et al. | |
| 2007/0276309 A1 | 11/2007 | Xu et al. | |
| 2007/0293830 A1 | 12/2007 | Martin | |
| 2008/0004549 A1 | 1/2008 | Anderson et al. | |
| 2008/0060550 A1 | 3/2008 | Macdonald et al. | |
| 2008/0071216 A1 | 3/2008 | Locke et al. | |
| 2008/0077091 A1 | 3/2008 | Mulligan | |
| 2008/0082059 A1 | 4/2008 | Fink et al. | |
| 2008/0089173 A1 | 4/2008 | Lu et al. | |
| 2008/0119802 A1* | 5/2008 | Riesinger | A61F 13/05 604/313 |
| 2008/0167593 A1 | 7/2008 | Fleischmann | |
| 2008/0171958 A1* | 7/2008 | Gundersen | A61F 13/022 602/56 |
| 2008/0200857 A1 | 8/2008 | Lawhorn | |
| 2008/0200906 A1 | 8/2008 | Sanders et al. | |
| 2008/0206155 A1 | 8/2008 | Tamarkin et al. | |
| 2008/0208147 A1 | 8/2008 | Argenta et al. | |
| 2008/0208163 A1 | 8/2008 | Wilkie | |
| 2008/0223378 A1 | 9/2008 | Henderson et al. | |
| 2008/0234641 A1 | 9/2008 | Locke et al. | |
| 2008/0243096 A1 | 10/2008 | Svedman | |
| 2008/0254103 A1 | 10/2008 | Harris et al. | |
| 2008/0287880 A1 | 11/2008 | Keller | |
| 2008/0294127 A1 | 11/2008 | Blott et al. | |
| 2008/0294147 A1 | 11/2008 | Radl et al. | |
| 2008/0300555 A1 | 12/2008 | Olson et al. | |
| 2008/0314929 A1 | 12/2008 | Keller | |
| 2009/0020561 A1 | 1/2009 | Keller | |
| 2009/0022779 A1 | 1/2009 | Kelly et al. | |
| 2009/0030086 A1 | 1/2009 | Eady et al. | |
| 2009/0093550 A1 | 4/2009 | Rolfes et al. | |
| 2009/0098073 A1 | 4/2009 | Macdonald et al. | |
| 2009/0134186 A1 | 5/2009 | Keller | |
| 2009/0157017 A1 | 6/2009 | Ambrosio | |
| 2009/0196844 A1 | 8/2009 | Choi et al. | |
| 2009/0204085 A1* | 8/2009 | Biggie | A61M 1/915 604/313 |
| 2009/0216170 A1 | 8/2009 | Robinson et al. | |
| 2009/0227969 A1 | 9/2009 | Jaeb et al. | |
| 2009/0234306 A1 | 9/2009 | Vitaris | |
| 2009/0234309 A1 | 9/2009 | Vitaris et al. | |
| 2009/0240185 A1 | 9/2009 | Jaeb et al. | |
| 2009/0275872 A1 | 11/2009 | Addison et al. | |
| 2009/0299251 A1 | 12/2009 | Buan | |
| 2009/0299255 A1 | 12/2009 | Kazala, Jr. et al. | |
| 2009/0299306 A1 | 12/2009 | Buan | |
| 2010/0022972 A1 | 1/2010 | Lina et al. | |
| 2010/0030132 A1 | 2/2010 | Niezgoda et al. | |
| 2010/0036305 A1 | 2/2010 | Green | |
| 2010/0069858 A1 | 3/2010 | Olson | |
| 2010/0122417 A1 | 5/2010 | Vrzalik et al. | |
| 2010/0125258 A1 | 5/2010 | Coulthard et al. | |
| 2010/0185163 A1* | 7/2010 | Heagle | A61F 13/05 604/290 |
| 2010/0210986 A1 | 8/2010 | Sanders et al. | |
| 2010/0230467 A1 | 9/2010 | Criscuolo et al. | |
| 2010/0262090 A1 | 10/2010 | Riesinger | |
| 2010/0262091 A1 | 10/2010 | Larsson | |
| 2010/0262092 A1* | 10/2010 | Hartwell | A61F 13/023 604/304 |
| 2010/0262096 A1* | 10/2010 | Hall | A61F 13/0203 604/319 |
| 2010/0262106 A1* | 10/2010 | Hartwell | A61F 13/36 87/8 |
| 2010/0268176 A1 | 10/2010 | Johnson et al. | |
| 2010/0268177 A1* | 10/2010 | Hall | A61M 1/90 604/319 |
| 2010/0268198 A1 | 10/2010 | Buan et al. | |
| 2010/0280469 A1* | 11/2010 | Hall | A61M 1/915 604/319 |
| 2010/0305526 A1 | 12/2010 | Robinson et al. | |
| 2010/0324510 A1 | 12/2010 | Andresen et al. | |
| 2011/0004172 A1 | 1/2011 | Eckstein et al. | |
| 2011/0021431 A1 | 1/2011 | Jones et al. | |
| 2011/0028918 A1 | 2/2011 | Hartwell | |
| 2011/0028919 A1 | 2/2011 | Johnnison et al. | |
| 2011/0028920 A1 | 2/2011 | Johannison | |
| 2011/0033503 A1 | 2/2011 | Sinko et al. | |
| 2011/0054421 A1 | 3/2011 | Hartwell | |
| 2011/0054423 A1 | 3/2011 | Blott et al. | |
| 2011/0086077 A1 | 4/2011 | McCrea et al. | |
| 2011/0118683 A1 | 5/2011 | Weston | |
| 2011/0172615 A2 | 7/2011 | Greener | |
| 2011/0172617 A1 | 7/2011 | Riesinger | |
| 2011/0224631 A1 | 9/2011 | Simmons et al. | |
| 2011/0282309 A1 | 11/2011 | Adie et al. | |
| 2012/0004631 A9* | 1/2012 | Hartwell | A61F 13/36 87/8 |
| 2012/0041399 A1 | 2/2012 | Blott et al. | |
| 2012/0053538 A1 | 3/2012 | Blott et al. | |
| 2012/0095380 A1 | 4/2012 | Gergely et al. | |
| 2012/0109085 A1 | 5/2012 | McNeil | |
| 2012/0116334 A1* | 5/2012 | Albert | A61F 13/022 604/319 |
| 2012/0130332 A1 | 5/2012 | Cotton et al. | |
| 2013/0090616 A1 | 4/2013 | Neubauer | |

(56) References Cited

U.S. PATENT DOCUMENTS

| | | | |
|---|---|---|---|
| 2013/0096518 A1* | 4/2013 | Hall | A61M 1/92 604/319 |
| 2013/0116635 A1 | 5/2013 | Fleischmann | |
| 2013/0123723 A1 | 5/2013 | Tout et al. | |
| 2013/0138054 A1 | 5/2013 | Fleischmann | |
| 2013/0144230 A1 | 6/2013 | Wu et al. | |
| 2013/0150814 A1 | 6/2013 | Buan | |
| 2013/0165878 A1 | 6/2013 | Heagle | |
| 2013/0261576 A1 | 10/2013 | Strobech et al. | |
| 2013/0267921 A1 | 10/2013 | Weston | |
| 2013/0274688 A1 | 10/2013 | Weston | |
| 2014/0018753 A1 | 1/2014 | Joshi et al. | |
| 2014/0039423 A1 | 2/2014 | Riesinger | |
| 2014/0114263 A1 | 4/2014 | Weston | |
| 2014/0114268 A1 | 4/2014 | Auguste et al. | |
| 2014/0135721 A1 | 5/2014 | Riesinger | |
| 2014/0188059 A1 | 7/2014 | Robinson et al. | |
| 2014/0330224 A1* | 11/2014 | Albert | A61F 13/0206 604/319 |
| 2014/0343519 A1 | 11/2014 | Weston | |
| 2015/0100045 A1* | 4/2015 | Allen | A61M 1/984 604/543 |
| 2015/0141941 A1* | 5/2015 | Allen | A61F 13/022 604/319 |
| 2015/0173954 A1 | 6/2015 | Blott et al. | |
| 2015/0209492 A1 | 7/2015 | Blott et al. | |
| 2017/0007753 A1 | 1/2017 | Blott et al. | |
| 2017/0156967 A1 | 6/2017 | Blott et al. | |
| 2019/0099293 A1* | 4/2019 | Hall | A61F 13/05 |

FOREIGN PATENT DOCUMENTS

| | | |
|---|---|---|
| DE | 3935818 A1 | 5/1991 |
| DE | 4016034 A1 | 11/1991 |
| DE | 19844355 A1 | 4/2000 |
| DE | 20301859 U1 | 4/2003 |
| DE | 202004018245 U1 | 7/2005 |
| EP | 0171268 A2 | 2/1986 |
| EP | 0521434 A1 | 1/1993 |
| EP | 0575090 A1 | 12/1993 |
| EP | 0669463 A2 | 8/1995 |
| EP | 0733375 A2 | 9/1996 |
| EP | 0858810 A2 | 8/1998 |
| EP | 0888141 A1 | 1/1999 |
| EP | 1007015 A1 | 6/2000 |
| EP | 1013290 A1 | 6/2000 |
| EP | 1029585 A1 | 8/2000 |
| EP | 1105171 A2 | 6/2001 |
| EP | 1105180 A1 | 6/2001 |
| EP | 1107813 A1 | 6/2001 |
| EP | 1030657 B1 | 10/2001 |
| EP | 1306123 A1 | 5/2003 |
| EP | 1440737 A1 | 7/2004 |
| EP | 1790378 A1 | 5/2007 |
| EP | 1880840 A1 | 1/2008 |
| EP | 1476217 B1 | 3/2008 |
| EP | 1923077 A1 | 5/2008 |
| EP | 2068257 A1 | 6/2009 |
| EP | 2111804 A2 | 10/2009 |
| EP | 2218431 A2 | 8/2010 |
| EP | 2462908 A1 | 6/2012 |
| FR | 1163907 A | 10/1958 |
| GB | 236350 A | 7/1925 |
| GB | 1334840 A | 10/1973 |
| GB | 1394171 A | 5/1975 |
| GB | 1400124 A | 7/1975 |
| GB | 1422171 A | 1/1976 |
| GB | 2037150 A | 7/1980 |
| GB | 1575266 A | 9/1980 |
| GB | 2047438 A | 11/1980 |
| GB | 2194446 A | 3/1988 |
| GB | 2235877 A | 3/1991 |
| GB | 2288734 A | 11/1995 |
| GB | 2307180 A | 5/1997 |
| GB | 2336546 A | 10/1999 |
| GB | 2371490 A | 7/2002 |
| GB | 2378392 A | 2/2003 |
| GB | 2378734 A | 2/2003 |
| GB | 2382989 A | 6/2003 |
| GB | 2418738 A | 4/2006 |
| GB | 2424582 A | 10/2006 |
| GB | 2435419 A | 8/2007 |
| JP | S6180018 U | 5/1986 |
| JP | 2005334188 A | 12/2005 |
| SU | 1578150 A1 | 7/1990 |
| WO | WO-9100718 A1 | 1/1991 |
| WO | WO-9209301 A1 | 6/1992 |
| WO | WO-9209651 A1 | 6/1992 |
| WO | WO-9212369 A1 | 7/1992 |
| WO | WO-9306802 A1 | 4/1993 |
| WO | WO-9309176 A2 | 5/1993 |
| WO | WO-9324083 A1 | 12/1993 |
| WO | WO-9420133 A1 | 9/1994 |
| WO | WO-9503018 A1 | 2/1995 |
| WO | WO-9640174 A1 | 12/1996 |
| WO | WO-9703717 A1 | 2/1997 |
| WO | WO-9711658 A1 | 4/1997 |
| WO | WO-9733922 A1 | 9/1997 |
| WO | WO-9742986 A1 | 11/1997 |
| WO | WO-9803267 A1 | 1/1998 |
| WO | WO-9806444 A1 | 2/1998 |
| WO | WO-9846818 A1 | 10/1998 |
| WO | WO-9901173 A1 | 1/1999 |
| WO | WO-9917698 A1 | 4/1999 |
| WO | WO-9919013 A1 | 4/1999 |
| WO | WO-9930629 A1 | 6/1999 |
| WO | WO-9947097 A2 | 9/1999 |
| WO | WO-9965536 A1 | 12/1999 |
| WO | WO-0017968 A1 | 3/2000 |
| WO | WO-0038752 A1 | 7/2000 |
| WO | WO-0061206 A1 | 10/2000 |
| WO | WO-0062827 A2 | 10/2000 |
| WO | WO-0064396 A1 | 11/2000 |
| WO | WO-0113853 A1 | 3/2001 |
| WO | WO-0162312 A1 | 8/2001 |
| WO | WO-0166017 A1 | 9/2001 |
| WO | WO-0185248 A1 | 11/2001 |
| WO | WO-0202079 A1 | 1/2002 |
| WO | WO-02083046 A1 | 10/2002 |
| WO | WO-02094256 A1 | 11/2002 |
| WO | WO-02102864 A1 | 12/2002 |
| WO | WO-03005943 A2 | 1/2003 |
| WO | WO-03022333 A1 | 3/2003 |
| WO | WO-03053346 A2 | 7/2003 |
| WO | WO-03057307 A1 | 7/2003 |
| WO | WO-03065877 A2 | 8/2003 |
| WO | WO-03073970 A1 | 9/2003 |
| WO | WO-03074100 A1 | 9/2003 |
| WO | WO-03101508 A2 | 12/2003 |
| WO | WO-2004016313 A1 | 2/2004 |
| WO | WO-2004018020 A1 | 3/2004 |
| WO | WO-2004037334 A1 | 5/2004 |
| WO | WO-2004054632 A1 | 7/2004 |
| WO | WO-2005006975 A1 | 1/2005 |
| WO | WO-2005009488 A2 | 2/2005 |
| WO | WO-2005017000 A1 | 2/2005 |
| WO | WO-2005018695 A1 | 3/2005 |
| WO | WO-2005046760 A1 | 5/2005 |
| WO | WO-2005046761 A1 | 5/2005 |
| WO | WO-2005046762 A1 | 5/2005 |
| WO | WO-2005082435 A1 | 9/2005 |
| WO | WO-2005091884 A2 | 10/2005 |
| WO | WO-2005102415 A1 | 11/2005 |
| WO | WO-2005105176 A1 | 11/2005 |
| WO | WO-2005105180 A1 | 11/2005 |
| WO | WO-2005118011 A1 | 12/2005 |
| WO | WO-2005123170 A1 | 12/2005 |
| WO | WO-2006014534 A2 | 2/2006 |
| WO | WO-2006030054 A1 | 3/2006 |
| WO | WO-2006034128 A2 | 3/2006 |
| WO | WO-2006052745 A2 | 5/2006 |
| WO | WO-2006052839 A2 | 5/2006 |
| WO | WO-2006056294 A1 * | 6/2006 ....... A61F 13/00068 |

(56) References Cited

FOREIGN PATENT DOCUMENTS

| | | |
|---|---|---|
| WO | WO-2006089551 A1 | 8/2006 |
| WO | WO-2006100053 A2 | 9/2006 |
| WO | WO-2006114638 A2 | 11/2006 |
| WO | WO-2006135506 A2 | 12/2006 |
| WO | WO-2007003905 A1 | 1/2007 |
| WO | WO-2007013064 A1 | 2/2007 |
| WO | WO-2007019038 A2 | 2/2007 |
| WO | WO-2007030598 A2 | 3/2007 |
| WO | WO-2007030599 A2 | 3/2007 |
| WO | WO-2007031765 A1 | 3/2007 |
| WO | WO-2007050594 A2 | 5/2007 |
| WO | WO-2007062024 A1 | 5/2007 |
| WO | WO-2007085396 A1 | 8/2007 |
| WO | WO-2007087808 A1 | 8/2007 |
| WO | WO-2007087809 A1 | 8/2007 |
| WO | WO-2007092397 A2 | 8/2007 |
| WO | WO-2007106594 A2 | 9/2007 |
| WO | WO-2007124198 A2 | 11/2007 |
| WO | WO-2007133618 A2 | 11/2007 |
| WO | WO-2007133644 A2 | 11/2007 |
| WO | WO-2008014358 A2 | 1/2008 |
| WO | WO-2008036345 A1 | 3/2008 |
| WO | WO-2008041926 A1 | 4/2008 |
| WO | WO-2008076407 A2 | 6/2008 |
| WO | WO-2008082444 A2 | 7/2008 |
| WO | WO-2008100437 A1 | 8/2008 |
| WO | WO-2008129318 A2 | 10/2008 |
| WO | WO-2008131895 A1 | 11/2008 |
| WO | WO-2008131896 A1 | 11/2008 |
| WO | WO-2008134544 A1 | 11/2008 |
| WO | WO-2008134774 A2 | 11/2008 |
| WO | WO-2008141228 A1 | 11/2008 |
| WO | WO-2008141470 A1 | 11/2008 |
| WO | WO-2009019227 A2 | 2/2009 |
| WO | WO-2009019229 A2 | 2/2009 |
| WO | WO-2009034322 A3 | 3/2009 |
| WO | WO-2009042514 A1 | 4/2009 |
| WO | WO-2009047524 A2 | 4/2009 |
| WO | WO-2009052193 A1 | 4/2009 |
| WO | WO-2009060327 A2 | 5/2009 |
| WO | WO-2009062327 A1 | 5/2009 |
| WO | WO-2009066106 A1 | 5/2009 |
| WO | WO-2009068666 A2 | 6/2009 |
| WO | WO-2009070905 A1 | 6/2009 |
| WO | WO-2009078790 A1 | 6/2009 |
| WO | WO-2009103031 A1 | 8/2009 |
| WO | WO-2009124100 A1 | 10/2009 |
| WO | WO-2009126102 A1 | 10/2009 |
| WO | WO-2009126833 A2 | 10/2009 |
| WO | WO-2009145703 A1 | 12/2009 |
| WO | WO-2009146441 A1 | 12/2009 |
| WO | WO-2009156709 A1 | 12/2009 |
| WO | WO-2009158128 A2 | 12/2009 |
| WO | WO-2010033271 A1 | 3/2010 |
| WO | WO-2010051068 A1 | 5/2010 |
| WO | WO-2010142959 A2 | 12/2010 |
| WO | WO-2010147533 A1 | 12/2010 |
| WO | WO-2012131237 A1 | 10/2012 |
| WO | WO-2012140378 A1 | 10/2012 |
| WO | WO-2012146656 A1 | 11/2012 |
| WO | WO-2013010907 A1 | 1/2013 |
| WO | WO-2013083800 A1 | 6/2013 |
| WO | WO-2014016759 A1 | 1/2014 |
| WO | WO-2014020440 A1 | 2/2014 |
| WO | WO-2014020443 A2 | 2/2014 |
| WO | WO-2014108476 A1 | 7/2014 |
| WO | WO-2014113253 A1 | 7/2014 |

OTHER PUBLICATIONS

Communication pursuant to Article 94(3) EPC for Application No. 08855752.5, mailed Mar. 9, 2012, 8 pages.
Communication pursuant to Article 94(3) EPC for Application No. 08856241.8, mailed Jul. 25, 2013, 3 pages.
Communication pursuant to Article 94(3) EPC for Application No. 08856241.8, mailed Mar. 8, 2011, 4 pages.
Communication pursuant to Article 94(3) EPC for Application No. 08856566.8, mailed Dec. 8, 2011, 4 pages.
Communication pursuant to Article 94(3) EPC for Application No. 08857939.6, mailed Mar. 8, 2011, 4 pages.
Communication pursuant to Article 94(3) EPC for Application No. 08857939.6, mailed Oct. 29, 2013, 3 pages.
English Translation of First Chinese Office Action for Chinese Application No. 200880117224.3 dated Jul. 4, 2012, 4 pages.
Info V.A.C. User Manual, KCI on Dec. 1, 2006 in 76 pages.
International Preliminary Report on Patentability for Application No. PCT/GB2008/051070, mailed on Jun. 8, 2010, 5 pages.
International Preliminary Report on Patentability for Application No. PCTGB2008/051075, mailed on Jun. 8, 2010, 7 pages.
International Preliminary Report on Patentability for Application No. PCT/GB2008/051114, mailed on Jun. 8, 2010.
International Preliminary Report on Patentability for Application No. PCT/GB2008/051122, mailed on Jun. 8, 2010, 5 pages.
International Preliminary Report on Patentability for Application No. PCT/GB2008/051134, mailed on Jun. 8, 2010, 6 pages.
International Search Report for Application No. PCT/GB2008/051070, mailed on Feb. 27, 2009, 2 pages.
International Search Report for Application No. PCT/GB2008/051134 mailed on Apr. 3, 2009, 4 pages.
International Search Report for Application No. PCT/GB2008/051122, mailed on Feb. 27, 2009, 2 pages.
International Search Report for PCT Application No. PCT/GB2008/051075, mailed on Mar. 11, 2009, 2 pages.
Internationl Search Report for Application No. PCT/GB2008/051114, mailed on Apr. 8, 2009, 5 pages.
Landis E.M., et al., "The Effects of Alternate Suction and Pressure on Blood Flow to the Lower Extremities," Alternate Suction and Pressure, J Clin Invest, Sep. 1993, vol. 12 (5), pp. 925-961.
Mitchell R.N., et al., "Role of Stem Cells in Tissue Homeostasis," Pocket Companion to Robbins and Cotran Pathologic Basis of Disease, 7th Edition, 2006, p. 55 (3 pages).

* cited by examiner

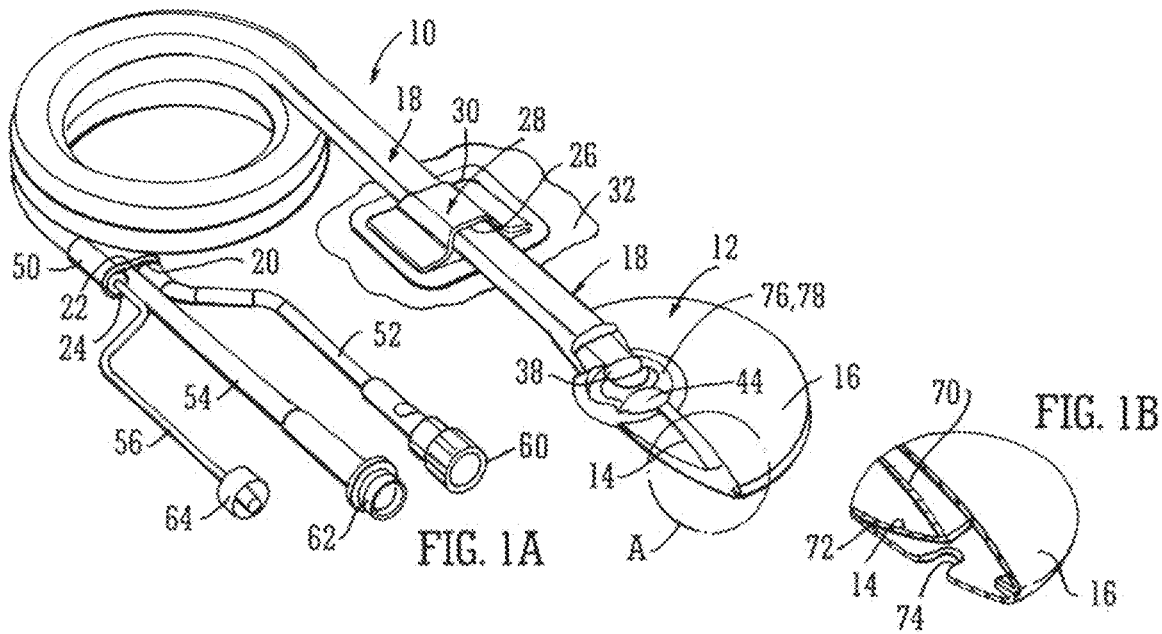
FIG. 1A
FIG. 1B
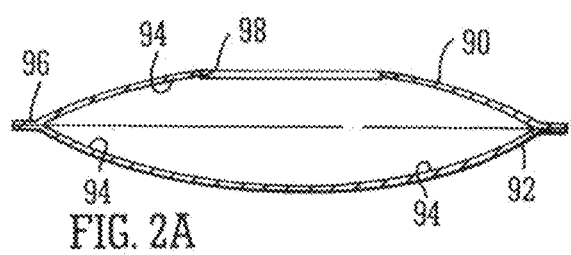
FIG. 2A
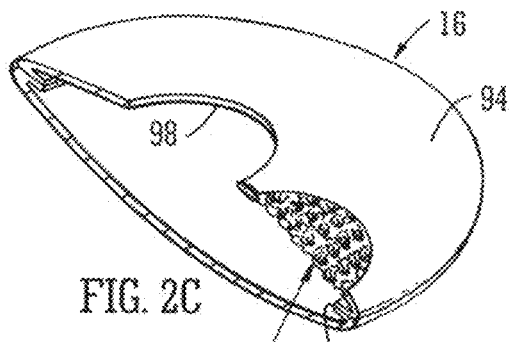
FIG. 2C
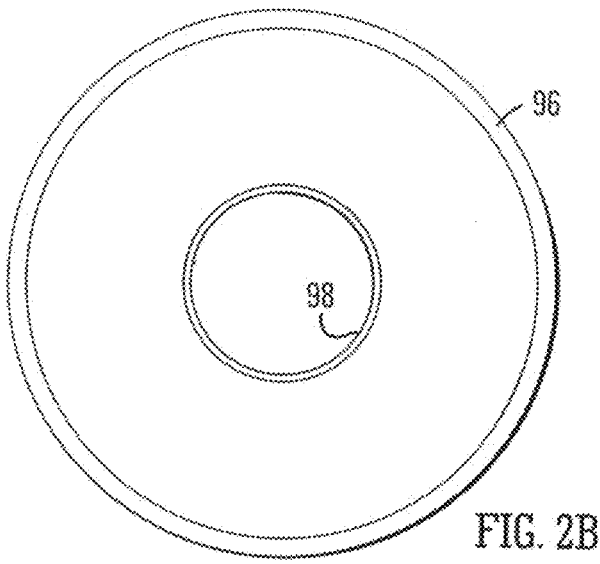
FIG. 2B
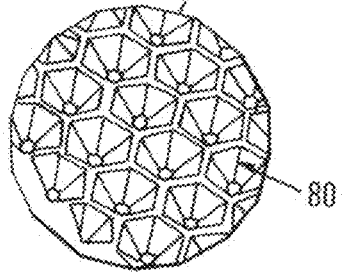
FIG. 2D

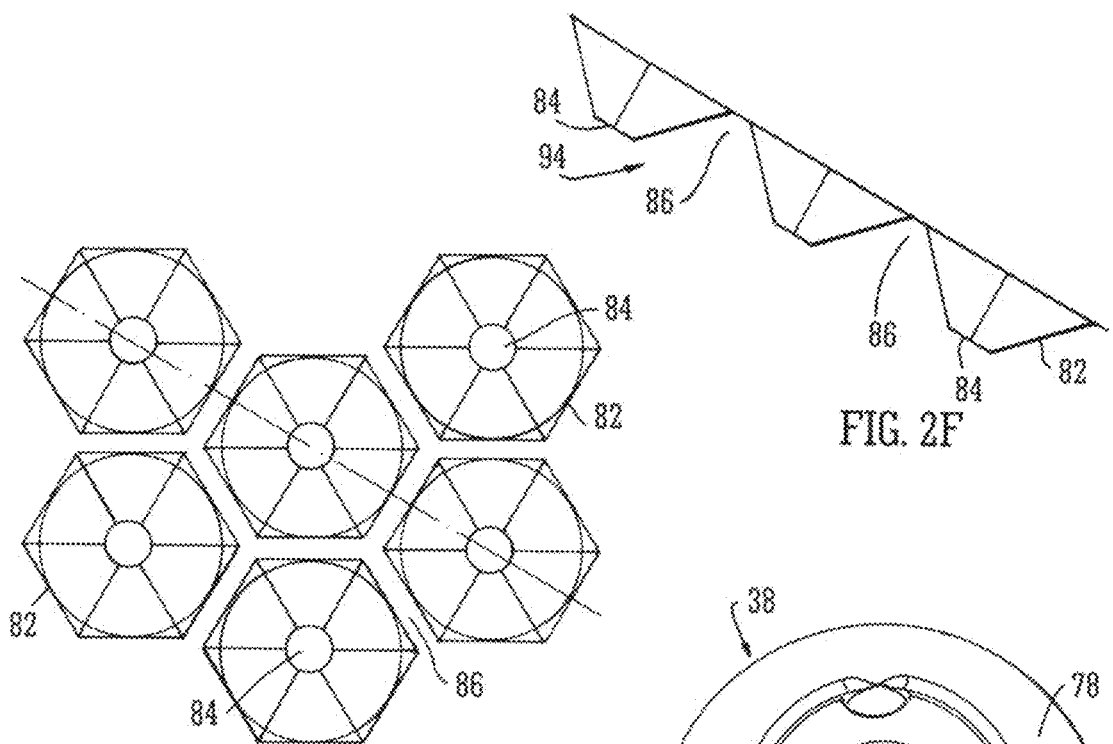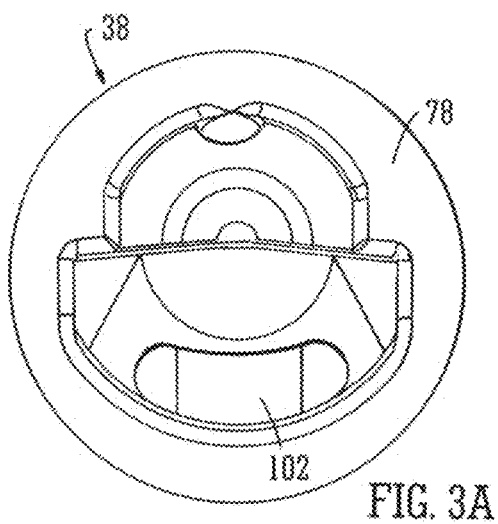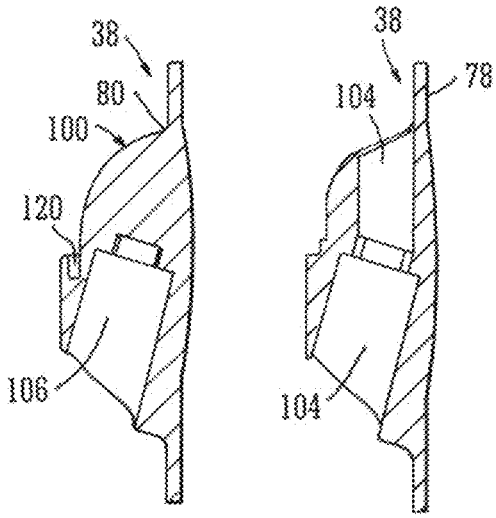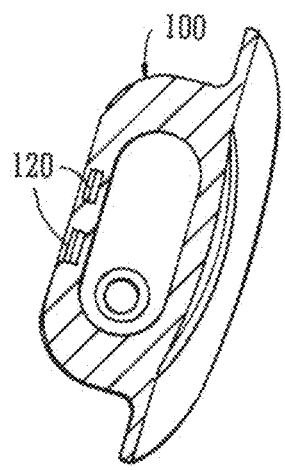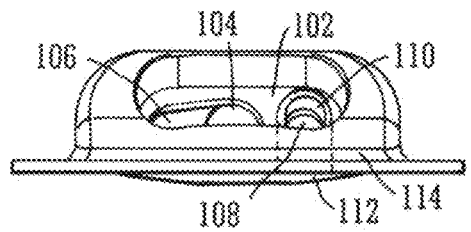

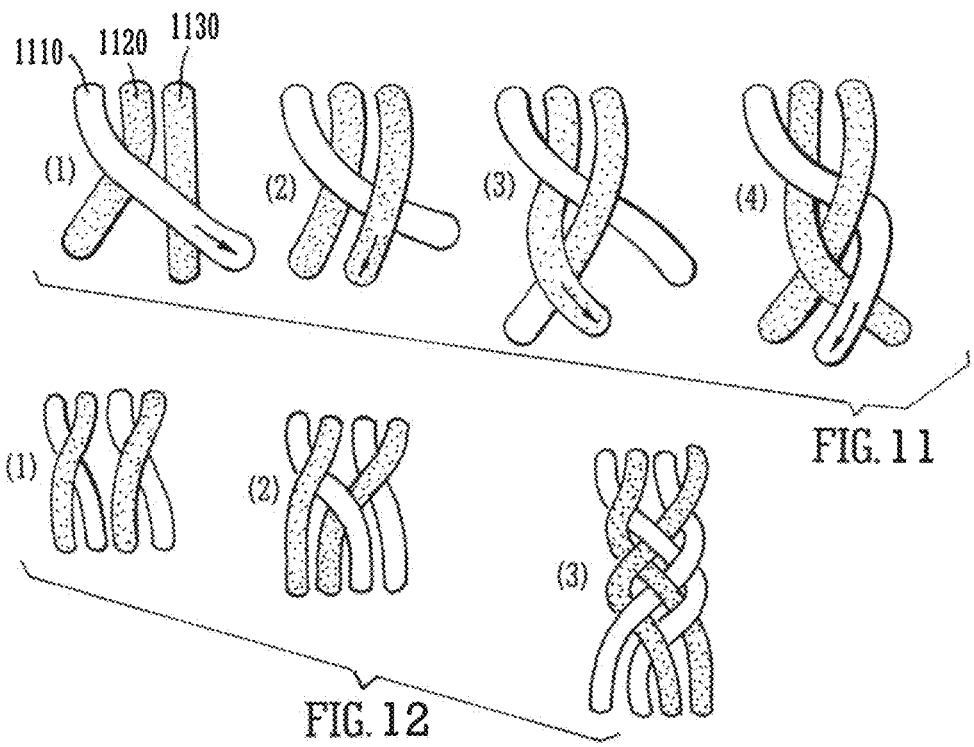
FIG. 11
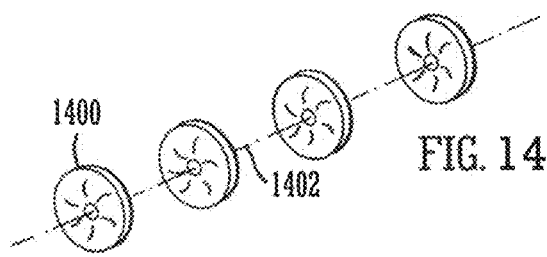
FIG. 12
FIG. 14
FIG. 13
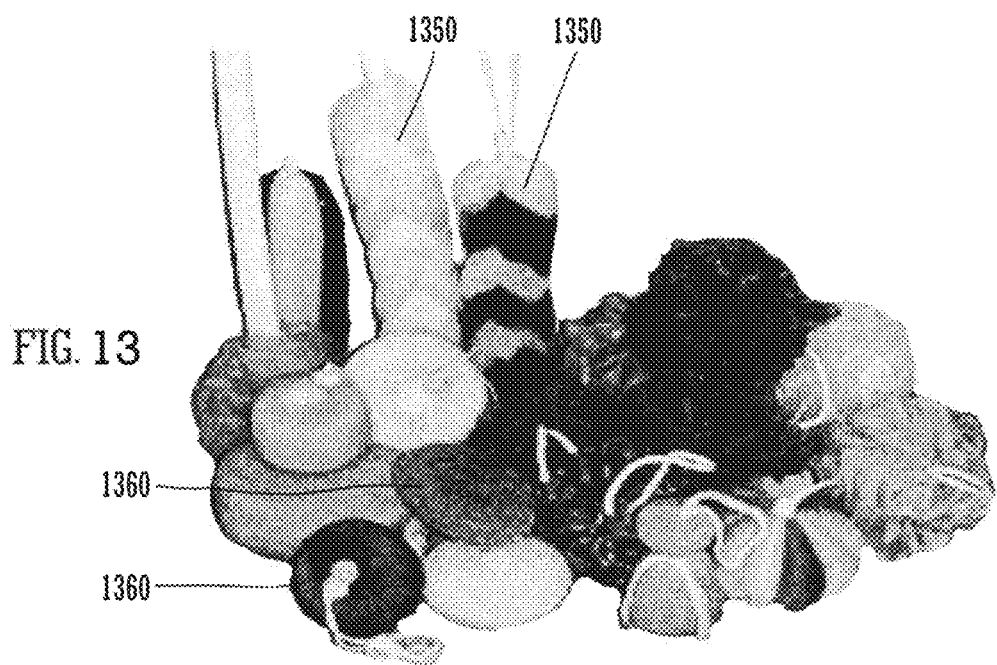

WOUND FILLING APPARATUSES AND METHODS

CROSS-REFERENCE TO RELATED APPLICATIONS

This application is a continuation of U.S. application Ser. No. 16/115,064, filed Aug. 28, 2018, which is a continuation of U.S. application Ser. No. 14/855,214, filed Sep. 15, 2015, which is a divisional of U.S. application Ser. No. 13/545,942, filed Jul. 10, 2012, which is a continuation-in-part of U.S. application Ser. No. 12/746,504, filed Jun. 4, 2010, which is a U.S. National Phase of PCT International Application No. PCT/GB2008/051114, filed on Nov. 26, 2008, designating the United States and published on Jun. 11, 2009 as WO 2009/071932, which claims priority to Great Britain Patent Application No. 0723874.4, filed Dec. 6, 2007. This application is also a continuation-in-part of U.S. application Ser. No. 12/746,508, filed Jun. 4, 2010, which is a U.S. National Phase of PCT International Application No. PCT/GB2008/051122, filed on Nov. 26, 2008, designating the United States and published on Jun. 11, 2009 as WO 2009/071935, which claims priority to Great Britain Patent Application No. 0723852.0, filed Dec. 6, 2007. This application is also a continuation-in-part of U.S. application Ser. No. 12/746,757, filed Jun. 7, 2010, which is a U.S. National Phase of PCT International Application No. PCT/GB2008/051075, filed on Nov. 17, 2008, designating the United States and published on Jun. 11, 2009 as WO 2009/071929, which claims priority to Great Britain Patent Application No. 0724044.3, filed Dec. 8, 2007. This application is also a continuation-in-part of U.S. application Ser. No. 12/746,753, filed Jun. 7, 2010, which is a U.S. National Phase of PCT International Application No. PCT/GB2008/051134, filed on Nov. 28, 2008, designating the United States and published on Jun. 11, 2009 as WO 2009/071938, which claims priority to Great Britain Patent Application No. 0724040.1, filed Dec. 8, 2007. This application is also a continuation-in-part of U.S. application Ser. No. 12/746,751, filed Jun. 7, 2010, which is a U.S. National Phase of PCT International Application No. PCT/GB2008/051070, filed on Nov. 17, 2008, designating the United States and published on Jun. 11, 2009 as WO 2009/071928, which claims priority to Great Britain Patent Application No. 0724039.3, filed Dec. 8, 2007. The disclosures of these prior applications are hereby incorporated by reference in their entireties and should be considered a part of this specification.

BACKGROUND OF THE INVENTION

Field of the Invention

Embodiments of the present invention relate to apparatuses, methods, devices, and systems for use in the treatment of wounds by topical negative pressure (TNP) therapy.

In recent years TNP therapy has become increasingly important in the field of improved treatment of wounds by making the healing thereof faster and more controlled.

The basic principle of TNP therapy is to create a closed cavity over the wound itself by means of a thin, flexible sealing film adhered to the patient's sound skin surrounding the wound; admitting one end of an aspirant conduit into the closed cavity, the conduit being sealed to the flexible film, for example; and connecting a distal end of the aspirant conduit to a vacuum source such as an electrically driven vacuum pump, for example, to create a pressure lower than the surrounding ambient atmospheric pressure within the wound cavity. As is known to the skilled person the lower pressure creates many beneficial therapeutic effects on the wound including increased blood flow to the wound and faster granulation of tissue, for example. There are very many variations on this basic principle of TNP therapy.

The types of wounds treated by TNP therapy generally range from quite small at about 5 cm$^2$ to very large traumatic wounds and burns of no particular maximum dimension. Such wounds may also have significant depth and therefore, significant volume. It is necessary to control the way in which a wound heals. For example, the wound should heal from the base up and close in from the edges desirably in a uniform manner. In particular it is desirable that the wound does not close over and form an occluded cavity in the flesh which is extremely undesirable from the patient's point of view as such form sites for infection.

To prevent the formation of occluded cavities during TNP therapy, the wound is usually packed with a filler which desirably has some resilience or "bounce" to resist the compressive forces created during TNP therapy by outside ambient atmospheric pressure bearing down on the wound due to the vacuum created in the wound cavity. The purpose of the filler is to keep the surrounding edges of the wound apart so that they cannot grow over and form a cavity. The filler may also perform the function of providing fluid flow channels between the wound and the filler in order to provide a uniform reduced pressure distribution over the surface area of the wound and to promote efficient aspiration of exudate fluids away from the wound surface and generally into a remote waste receptacle associated with the aspirant conduit.

As noted above there are very many variations on the basic TNP therapy principle and to illustrate how complex TNP therapy may be reference is made to the documents described below and which are of common ownership herewith.

TNP therapy often involves the provision within a dressing to which a negative or a positive pressure is applied a bag member (sometimes also referred to as a bladder) which may be used to at least partially fill a volume of a wound, for example. Furthermore, fluctuating pressure or pressure cycling may be applied to the bag member in order to work the tissue in and around the wound region for therapeutic reasons, for example.

There are many commercially available bag members which may be included in a wound dressing, however, commercially available bag members suffer from the disadvantage that they are obviously of predetermined size and shape, for example, and there may not be available a bag member of a corresponding form to that of the wound which needs treatment. Such unavailability may not be just the unavailability in the particular hospital formulary or store, for example, but a suitably sized and shaped bag member may not be available at all commercially.

Description of the Related Art

In International patent application, WO 2004/037334, apparatus, a wound dressing and a method for aspirating, irrigating and cleansing wounds are described. In very general terms, this application describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In International patent application, WO 2005/04670, apparatus, a wound dressing and a method for cleansing a wound using aspiration, irrigation and cleansing wounds are described. Again, in very general terms, this application utilises a similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The contents of the above references are hereby incorporated by reference in their entireties.

In spite of the self-evident growing complexity of TNP therapy, in general the field of wound fillers, which are a vital element in the therapy, has changed or improved very little over the years that TNP therapy has been developing. Aside from complicated and expensive inflatable bags, most of the fillers in use are based either on foam or on cotton gauze. Foam fillers are usually cut with scissors to the required shape (of the wound) by a clinician. However both foams and gauzes have the disadvantage that the cell or pore size is often too large and often results in growing tissue growing into the cells and adhering the foam to the wound causing further damage and trauma to the wound and patient on removal. When gauze is used as a filler, however, clinicians are instructed to "fluff up" the gauze to increase its volume which can cause problems in that the actual form of the gauze as packed into wounds is very variable. A further disadvantage with both foams and gauze when cut to fit wounds is that of debris. Gauze and foam are particularly prone to shedding fibres and particles when cut and these inevitably find their way into the wound and become occluded therein which can lead to later infection.

Foam or gauze as the wound filling medium has the additional disadvantage of tissue ingrowth into the pores of the filler and which may cause damage to newly formed granulation tissue on removal and also pain to the patient. Furthermore, such porous materials are subject to becoming saturated with wound exudate fluids causing a build up of bacteria leading to infection.

All of the wounds to which the above documents are addressed may require the provision of a bag member or bladder within a wound dressing and those currently available may be unsuitable. Indeed, International patent application WO 2004/037334 referred to above shows at FIGS. 13A and 20 embodiments employing pre-formed inflatable bladders used in apparatus for wound therapy.

Other reasons why inflatable bladder-type wound fillers may be used is to apply an uneven or textured or otherwise non-smooth surface possessed by the bladder surface directly onto a wound surface/interface. The textured surface assists in "working" the wound surface thereby enhancing the therapeutic effect of pressure cycling. A textured surface also provides a plurality of fluid flow channels at the interface between the wound filler and the wound surface to assist in a more even (negative) pressure distribution over the wound surface and a more rapid and even drainage of fluids such as wound exudates, for example, away from the wound region towards an aspiration conduit generally forming part of a TNP therapy apparatus.

Examples of known inflatable wound fillers are described in WO-A-2005/082435 and GB-A-2378392, the entireties of both of which are hereby incorporated by reference.

In WO-A-2005/082435, an inflatable bag or bladder-type wound filling member is used to fill the wound cavity. The bladder member is described as having two layers, however, the two layers appear to be in the form of an integral structure. A problem with this type of structure is that it is difficult and costly to manufacture. The structure also makes the bladder relatively rigid and stiff and inflexible against a wound surface possibly leading to discomfort and trauma.

GB-A-2378392 describes a wound irrigation and/or suction device comprising an inflatable bladder or pouch having a plurality of flexible conduits provided within and running through the bladder interior, the conduits having outlet/inlet apertures on the bladder surface. The conduits are fluid transfer conduits to either supply fluid to the wound or to conduct fluid away from the wound or both. However, a problem with this particular construction is that it is extremely complex and costly to manufacture.

It is an object of certain embodiments described herein to overcome or mitigate some of the disadvantages of known wound fillers.

It is further intended in certain embodiments to provide a method of making a suitably sized and shaped bag member in a dressing for a particular wound from materials commonly available in most hospital formularies or stores.

SUMMARY OF THE INVENTION

According to a first embodiment there is provided a wound filling device for use in an apparatus for the application of topical negative pressure therapy to a site on the body of a mammal, the device comprising: an inflatable bag member having at least one fluid carrying conduit operably connected thereto to inflate/deflate said bag member; a separate textured covering sock member at least partially covering the inflatable bag member.

The wound filling device as described above may form part of an apparatus for the application of TNP therapy to a wound, for example, on the body of a human being. Such apparatus may also generally include an aspiration conduit connected to aspiration means such as a vacuum pump, for example, for aspirating a wound cavity defined beneath a sealing membrane or drape covering adhered to sound skin or flesh surrounding the wound and beneath which the inflatable bag member and sock member are enclosed. The at least one conduit operably connected to the inflatable bag for inflating/deflating may also pass through or under the sealing membrane or drape but in any event be sealed thereto in accordance with well known TNP dressing structures. Provision of negative pressure may be achieved by any means or methods known in the art to evacuate the wound cavity region.

The inflatable bag member may be operably connected to a suitable means for inflation thereof via the at least one conduit. Such means may include well known types of pump able to pump inflation fluid, such as air for example, into the bag and also perhaps to suck fluid out so as to either maintain a constant pressure therein or to apply a pulsating pressure regime within the bag so as to work the wound surface to achieve beneficial therapeutic effects on the wound.

Whilst the option of positive pressure inflation of the bag member is described above there is also the option of allowing the bag member to self-inflate by leaving the conduit connected thereto open to atmosphere. As the wound cavity surrounding the bag member is evacuated by a vacuum pump, for example, the bag will tend to inflate by drawing air into it purely due to the pressure differential between the wound cavity and the bag interior as the bag surfaces are drawn towards the wound surface on one side and to the inner surface of the sealing drape membrane on the other side.

The wound cavity formed beneath the sealing membrane or drape may also have a further conduit provided thereto to supply an air bleed into the wound cavity so as to maintain a constant negative pressure therein to avoid undue discomfort to a patient due to excessive negative pressures being applied where the sealing membrane is particularly effective in sealing the wound cavity. Such a bleed conduit will also promote continuous aspiration of the wound cavity. Such an additional conduit may also serve the dual purpose of be used to measure pressure at the wound when a pressure transducer is connected to it distal to the wound.

A further conduit may be provided having access to the wound cavity region for the provision or application of an irrigant and/or medicaments to the wound site.

The inflatable bag member and the sock member may be mutually slideable relative to each other. Thus, as the bag member is inflated and deflated in a predetermined pressure pulsing regime, for example, the outer surface of the bag member and the inner surface of the sock member may slide against one another. This prevents the textured surface of the sock member from being forced to slide against the wound surface and causing possible trauma thereto and potentially damaging newly formed granulation tissue and thus, the outer textured surface of the sock member may apply pressure pulses substantially normally to the wound surface.

By providing the inflatable bag member and the textured sock member as two separate items made by known economic manufacturing techniques, several advantages are gained. Firstly, the inflatable bag member may be made from inherently soft and flexible thin sheet material which remains so even when having folds and convolutions when inside the wound cavity thereby imposing a minimum of unnecessary stress and trauma on the wound surface compared with known multi-layer bag constructions. The material from which the inflatable bag member may be made may be relatively very thin since the pressures which it is configured to withstand on inflation are relatively low. Secondly, by having a separate sock member over the inflatable bag member, the sock member surface texturing may be tailored to the requirements of the wound surface and have a suitable sock/wound interface design adapted to the wound type.

The sock member may be made from two sheets of material having substantially coterminous outer shapes, for example, and be welded together at their outer peripheries. One sheet may have an aperture, for example, in the centre through which the inflatable bag member is to be inserted, and also about which aperture the sock member may be turned inside out so as to contain the welded periphery on the inside of the sock member out of contact with the wound surface.

The inflatable bag member may be made from thin, flexible, substantially impervious plastics sheet material such as EVA, PU, PP, PE, silicone and any other suitable flexible plastics materials, for example, in similar manner to the sock member in that after welding it may be turned inside out to contain the weld on the inside. However, this is optional as the inflatable bag member is contained within the sock member so preventing the welded periphery from contacting the wound.

Thus, by having separate bag and sock members, the components may be made having properties which are optimised for its function and not compromised by having to fulfill two separate roles.

In one embodiment of an inflatable bag member and sock member the sheets from which they are made may be circular, for example.

The sock member may be moulded as an entity for subsequent combination with the inflatable bag member.

The conduit for inflating/deflating the bag member may be sealed to the bag member where it passes into the interior thereof. However, in a preferred embodiment, the inflatable bag member is provided with an aperture to which is affixed, by welding for example, a port member which may provide fluid access to the inflatable bag member and advantageously, fluid access to and from the wound cavity region. Such a port member may have provision for joining suitable fluid conduits such as flexible plastics materials conduits. The port member may also advantageously be provided with a suitable shroud member which serves the dual purpose of providing a smooth rounded surface which does not cause discomfort to a patient should it be lain upon and also maintaining a free flow of fluids from the wound site without the various ports being occluded or blocked by the overlying sealing drape membrane. The port member and shroud provides the advantage of having some or all of the conduits grouped together and being able to handle the group of conduits as one which makes application of the apparatus to a wound quicker and more efficient and improving the reliability of the TNP apparatus.

In a preferred embodiment, when in use, access of the various conduits to the wound cavity region below the sealing drape may be provided by a dressing and grommet combination as described in GB patent application 0712735.0 and PCT/US 2007/074374 of common ownership herewith, the entireties of which are hereby incorporated by reference.

The construction of the device according to one embodiment uses a soft and flexible sock material allows easier dressing removal since the sock may be made from material substantially non-adherent to the wound surface thus causing less distress and trauma to the patient.

The separate sock member embodiment promotes a reduction in tissue growth tending to close the wound and leave a cavity. The sock member effectively forms an analogous member to wound fillers in conventional TNP therapy of preventing wound overgrowth and minimising the formation of pockets within the tissue and encouraging the wound to heal by secondary intent or from the wound base upwards.

The textured surface of the sock member may primarily be present to provide a plurality of channels over the surface of the bag/sock combination so as to provide an even pressure distribution over the whole surface area of the wound and also to provide by the same plurality of channels efficient and rapid drainage of wound exudate fluids therefrom.

In one embodiment of a sock member the textured surface may comprise an array of hexagonal indentations or depressions in the sock material surface effectively producing a three-dimensional surface structure, some or all of the indentations or depressions having a perforation located substantially at its centre to allow fluid flow, both gaseous and liquid, over both surfaces of the sock member, i.e. between the wound surface and sock surface and between the inflatable bag surface and sock surface. A suitable material from which the sock member may be made may be a vacuum formed plastics sheet material such as, for example, EVA film which is soft and non-adherent to a wound surface.

The sock member may have any desired surface topography and formations which are conducive to wound surface therapy.

Alternative materials from which the separate sock member may be formed may comprise woven materials, non-woven fibrous sheet, foams, electrospun nano fibres from a wide variety of different materials such as EVA, PU, PP, PE, silicone, carbomethoxy cellulose, polyacrylate, for example.

Bio-degradable materials such as collagen, oxidized cellulose, chitosan, polyglycolic acid and the like may be used, for example.

In one embodiment the inflatable bag member, port and shroud members, conduits, an appropriate dressing and grommet member for attachment to a patient and sock member may be supplied as one integrated unit which merely needs to be applied to wound and connected to suitable sources of vacuum and inflation fluid to be put into effect as TNP therapy apparatus.

According a second embodiment there is provided a wound filling device comprising a non-porous bag member, the bag member being sealed against ingress of wound exudate and being filled with resilient, compressible material.

Desirably, the bag member may be provided with a surface texture such as may permit the provision of a uniform vacuum pressure distribution, when used in TNP therapy, over the surface of a wound bed and also allow wound exudate to be drawn from some or all parts of the wound bed towards an aspiration conduit so as to be removed from the site of a wound.

Suitable surface textures may be provided by, for example, but not limited to pimples, channels and ribs and the like formed on the bag member surface. The gaps and channels formed between protrusions of various types on the bag surface permit a uniform pressure distribution over the area of the wound bed and also provide fluid pathways to permit wound exudate to be drawn around the bag member rather than through it as with prior art wound fillers and be aspirated away from the wound site.

The textured surface also applies micro-stresses to the wound bed surface and which has been shown to stimulate tissue growth and wound healing.

Advantageously it has been found that fluid channels and pathways on the surface of the bag member may be of the order of about 0.5 to 2.0 mm with struts (i.e. ridge members, for example, between channels) of the order of 0.1 to 1.0 mm. A non-limiting example may be upstanding cylinders on the bag member surface of 0.2 mm diameter and 1 mm height and pitched centres of about 1 mm arranged in equilateral triangular repeated array.

Materials from which the bag member may be formed is desirably soft and conformable may suitably be selected from the group including: HDPE, PU such as Elastane SP806™, silicone, PVC and EVA, for example. The bag member may also be of laminated construction such as from, for example, Biobrane™ which comprises a layered structure of non-porous silicone rubber; a Nylon™ mesh adhered thereto; and collagen peptide particles impregnated into the Nylon fabric mesh surface which is placed adjacent the wound.

The bag member wound packing member may also advantageously be treated with biologically active components such as silver or in addition to or in substitution of silver, antimicrobial compounds (e.g. silver containing species, iodine, guanidines, biguanidines etc.), analgesics (e.g. aspirin, ibuprofen etc.), anaesthetics (e.g. amethocaine, lignocaine etc.), growth factors (e.g. VEGF, PDGF), vasodilators (e.g. NO, sildenafil, histamine etc.) for example. Other examples of suitable active components may be found in WO 2005/105180 the content of which is included herein by reference.

In some embodiments, the bag member of the wound filling devices may optionally be soaked or coated in a non-adherent gel such as, for example, a petroleum gel an example of which is Cuticerin™, silicone gel or a hydrogel.

The resilient, compressible filling of the bag member may comprise foam or polystyrene beads, for example, however any suitable material having the desired physical characteristics may be used as the bag filling material does not come into contact with wound exudate. The bag filing material should be relatively soft but hard enough to deflect skin/tissue in the wound bed so as to stress the tissue without being too aggressive. Suitably a material hardness in the region of 70 to 100 Shore may be employed. It has been found that a plain smooth bag even with the filling may not be able to resist being pressed down into intimate contact with the wound bed by the surrounding atmospheric pressure and occluding areas of the wound from the vacuum in the wound cavity.

In some embodiments the resilient, compressible filling in the bag member may be a gas such as air or nitrogen, for example, in order to save weight on a patient in the case of a large wound. In such cases it may be desirable for the surface texturing of the bag member to be more pronounced.

Some embodiments of wound filling devices may be made to work or stress a healing wound by cycling of the vacuum applied to the wound cavity resulting in the surrounding atmospheric pressure stressing the wound bed in a cyclic manner.

A plurality of wound filling devices may be joined together in a string and a suitable number to fill a given wound be cut off from the string. Suitable material with which to string a plurality of wound filling devices together may be nylon filament which does not shed debris in the wound. A particular advantage of the wound filling devices is that they are used as units and not sub-divided and do not like foams and gauzes shed debris into the wound when cut and which debris can be occluded in a healing wound and cause later infection.

Although the bag member is sealed against ingress of wound exudate, in an embodiment of a wound filling device, the interior of the bag member may be connected by a flexible conduit to a fluid reservoir outside the wound and the covering sealing drape. The reservoir may contain a heated fluid such as warm water, for example, which may be beneficial in terms of wound healing. Alternatively, the reservoir may contain a cooled fluid which in some circumstances may be more beneficial to the wound healing process. Some circulation of the fluid may be achieved by pressure cycling of the vacuum in the wound cavity which may cause fluid to be drawn into the bag member in one cycle and be expelled in the following cycle. Thus, if the fluid in the reservoir is temperature controlled so may the fluid in the bag member in the wound.

According to a third embodiment there is provided an apparatus for the application of topical negative pressure therapy to a site on the body of a mammal and which apparatus embodies the wound filling device of the first and/or second embodiments.

According to a fourth embodiment there is provided a method of making a three-dimensional wound packing member, the method comprising the steps of: taking material selected from at least one of the following forms comprising perforated sheet, net, woven, non-woven and knitted material; subjecting the at least one material to at least one forming process selected from the processes comprising rolling into tubes, braiding, knotting and knitting to form a three-dimensional and resilient structural unit member for packing into a wound.

Certain embodiments may also comprise a further step of linking together a plurality of the structural units so formed into a chain, for example, by thread means. The chain so formed may then be used to pack a wound for TNP therapy. However, if the chain so formed provides too much volume then it may be reduced by removing a suitable number of chain units until of the appropriate overall desired volume is achieved. The linking thread means may, for example, be a monofilament thread such as Nylon™, for example, so that cutting of the thread does not create any shedding or loose fibres.

Some embodiments comprise a method of making 3 dimensional wound packing means with variable pore size and compressibility from flat sheet material, for example. By taking sheet/net/woven/non-woven/knitted material and braiding, knotting or knitting and/or forming into tubes it is possible to create 3 dimensional structures with variable but controlled open volumes and densities. It is further possible to tie units of these structures so formed together into strings or chains with linking means to form larger structures. By changing the pore size, width of material between pores and thickness of the sheet/nets it is possible to vary the compressibility and pore size of the 3D structure. The user may vary the volume of the packer by adding suitable numbers of units of wound packing members together in a wound and in the case of strings may cut the appropriate volume of packing members at the linking entities. The packing members may be used as a general wound packer, or in conjunction with a sealing means and vacuum conduit as a packer for TNP therapy of wounds where it is essential that an even distribution of pressure takes place together with allowing for contraction of the wound, and intermittent contact of the wound with the packing member.

The selected material may be rolled, for example, into a tube or strand and that tube or strand with others may then be plaited, braided, knitted or woven for example, into a 3D structural member unit having controlled resilience and porosity. In an alternative structural wound packing member embodiment, a rolled tube of the selected material may then be further rolled along the axis of the tube in the manner of a ladies stocking, for example, so as to form a doughnut or ball shape depending upon the tightness of the starting rolled tube. A plurality of such doughnuts or balls formed in this manner may also be linked together to form a chain or string.

In some embodiments relating to linking a plurality of individual wound packing member units together, when a specific number of units is cut from a chain of units, then when these are removed from a wound at a time of dressing change then they may be removed together while reducing the likelihood of units remaining hidden in a deep wound, for example, as there is with a plurality of unconnected wound packing members.

An important advantage of certain embodiments of wound packing member units is that they may be made from materials which do not naturally adhere to a wound surface such as, for example, polyurethane, polypropylene, ethylvinylacetate, silicone and the like. Further advantages of such material are that they do not shed fibres or particles when formed as extruded sheet or thermo-bonded net.

The packing member units so formed may be engineered to provide desired characteristics of porosity, compressibility and volume by controlling the degree of porosity/perforation in the initial starting sheet, for example, then controlling the degree of tightness with which the sheet is rolled, for example, and then controlling the degree of tightness with which a plurality of the rolled tubes are then braided or plaited or knitted together, for example.

Compressibility of the types of material contemplated as wound packing members may typically lie in the range from 0.01 to 0.5 kgf/cm$^2$, preferably from 0.025 to 0.050 kgf/cm$^2$ when measured at a compression deflection point of 40% according to DIN 53577. The materials remain freely porous to the flow of wound exudate at a compression pressure of 0.16 kgf/cm$^2$. Typically a material would deflect to about 50% to 90% of the relaxed volume at a pressure of 0.16 kgf/cm$^2$ and recover to about 90% of the original volume upon pressure release.

Integrity of the braided, plaited, knitted wound packing member units may be preserved by the additional step of adhesively bonding, heat sealing or tying with monofilament thread the ends of the units to prevent unraveling, for example.

It is intended that wound packing unit members are used as formed and not subdivided by cutting into smaller units which would to an extent defeat the object of eliminating shedding of particles into a wound.

According to a fifth embodiment there is provided a three-dimensional wound packing member unit when made by the first aspect of the present invention.

According to a sixth embodiment there is provided a kit comprising a plurality of three-dimensional wound packing member units according to the second embodiment linked together by a thread.

According to a seventh embodiment there is provided a wound packing unit comprising a resilient, fluid absorbent material contained within a porous bag member, the porous bag member being made of a material which is non-adherent to the wound.

The resilient, fluid absorbent material may be any suitable known material such as gauze, foams and the like which are known for use in wound packing.

The porous bag member may be any suitable material known to be non-adherent to a wound and especially to new growing tissue. As noted above, one of the problems of using known gauzes and foams for wound packing or filling materials is that the pore sizes of the material often leads to in-growth of granulation tissue into the pores and which may be damaged on changing a wound dressing and also causing pain to the patient. The size of surface porosity of the bag member may be such that growing tissue does not grow into the surface pores and thus does not create a mechanical connection thereto. The material from which the porous bag member may be formed may be a suitable plastics sheet or net material such as EVA, PU, PP, PE, silicone, carbomethoxy cellulose, polyacrylate, for example.

The plastics sheet may comprise nets, woven materials, non-woven fibrous sheet, foams, electrospun nano fibres, for example, from a wide variety of different materials such as those noted above, for example.

A sheet film material may be configured with a certain level of porosity by perforating the sheet with any desired pattern or form of perforations.

The wound packing unit may be made from two sheets of suitable material having substantially coterminous outer shapes, for example, and be welded together at their outer peripheries so as to contain the resilient absorbent material in the cavity so formed. The bag member may comprise two sheets of material joined at their peripheries to form a pocket therein to receive the resilient, fluid absorbing material therein.

In one embodiment the sheets from which the wound packing units are made may be circular, for example.

Certain embodiments of a wound packing unit may be used as a general, stand-alone wound filling medium in the context of a dressing used for the treatment of any type of wound. Furthermore, the wound filling unit as defined is not used in a sub-divided form by, for example, cutting into a smaller member. A particular advantage of using the wound packing units as one or more units to fill a wound without cutting as with known wound packing materials such as gauze and foam on their own is that there is no shedding of particles due to cutting and consequently no occluded particles in the wound which may lead to infection.

Whilst the wound packing unit may be used singly or in a plurality thereof as general wound filling member(s) in any dressing where suitable, certain embodiments of a wound packing unit may advantageously be used as part of a wound dressing in TNP therapy. In such a dressing, the wound packing unit or plurality of them may be used to pack the wound and, the most basic form of TNP therapy, a covering film or drape adhered over the wound to the patient's sound flesh surrounding the wound in order to form a closed or sealed cavity over the wound, and an aspirant conduit connected to a vacuum source being admitted to the so-formed wound cavity.

When used as part of a dressing in TNP therapy the sheet material may desirably be textured so as to form channels in the surface adjacent the wound surface to further enhance the generation of an even negative pressure distribution over the surface of the wound and to enhance the flow and drainage of wound exudate to an aspirant conduit so that it may be aspirated from the wound vicinity into a remotely located waste receptacle. Whilst the filling of the bag member may be an absorbent material able to absorb wound exudate, it is nevertheless beneficial that as much of the exudate as possible is aspirated to a waste receptacle. In this way risk of infection due to build up of exudate may be minimised.

In one embodiment of a porous bag member the textured surface may comprise an array of hexagonal indentations or depressions in the bag material surface effectively producing a three-dimensional surface structure, some or all of the indentations or depressions having a perforation located substantially at its centre to allow fluid flow, both gaseous and liquid, over both surfaces of the bag member, i.e. between the wound surface and bag surface and between the bag surface and filling. A suitable material from which the bag member may be made may be a vacuum formed plastics sheet material such as, for example, EVA film which is soft and non-adherent to a wound surface.

The bag member may have any desired surface topography and formations which are conducive to wound surface therapy.

When used in TNP therapy, the bag member may have an aspirant conduit having a drain portion affixed during manufacture with its drain end inside the bag member and surrounded by the resilient absorbent filling. In this way time may be saved applying a TNP dressing and also the correct positioning of the aspirant conduit may be ensured.

The resilient absorbent filling material within the bag member may also be provided with antimicrobial additives such as silver, for example, to reduce or control bacterial load so as to control infection.

The resilient absorbent material filling of the wound packing unit may also advantageously be provided with other biologically active components in addition to or in substitution of silver, such as antimicrobial compounds (e.g. silver containing species, iodine, guanidines, biguanidines etc.), analgesics (e.g. aspirin, ibuprofen etc.), anaesthetics (e.g. amethocaine, lignocaine etc.), growth factors (e.g. VEGF, PDGF), vasodilators (e.g. NO, sildenafil, histamine etc.) for example. Other examples of suitable active components may be found in WO 2005/105180 the content of which is included herein by reference.

The sheet material of certain embodiments of wound packing units may optionally be soaked or coated in a non-adherent gel such as, for example, a petroleum gel an example of which is Cuticerin™, silicone gel or a hydrogel.

As with the filling the sheet material forming the porous bag member may also be treated with silver for antimicrobial purposes etc.

The resilient, fluid absorbent material within the porous bag member or the porous bag member itself may be formed from laminated material so as to provide a texture to the wound packing member unit. Such laminated material may have a "quilted" type of texture where two layers of material may be welded together in a pre-determined pattern with a layer of a resilient material such as an open cell polymer foam, for example, between. The two outer material layers of the laminate may be provided with an array of pores in predetermined fashion to permit ingress of exudate. Some cells formed by a laminating procedure may be left unperforated so as to provide resilience by virtue of compressing the air trapped inside unperforated pockets or cells so formed.

A porous bag member may be formed from two layers of laminated material as described above. Furthermore, a wound packing unit so formed may also further comprise resilient, fluid absorbent material therebetween.

The types of sealing film drapes generally used to form the overlying wound sealing medium in TNP dressings usually have a coating of adhesive over the whole surface of the film. Therefore, it may be desirable to place a second sheet of non-adhesively coated film between the sealing film drape and the wound packing unit so that when the sealing drape is removed as the first step of a dressing change the wound packing unit is not torn from the wound with it.

According to a seventh embodiment there is provided a method for packing a wound cavity comprising the steps of; forming a wound packing unit by enclosing a resilient absorbent material within a porous bag member, the porous bag member being made of a material which is non-adherent to the wound.

According to an eighth embodiment there is provided a dressing for the application of topical negative and/or positive pressure therapy to a wound, the dressing comprising in use: an optional layer of a pressure resistant porous material adjacent a surface of a wound to be treated; a first layer of a flexible wound covering and sealing material on top of the optional pressure resistant porous material adapted, in use, to surround the wound and seal against sound tissue to form, in use, a first sealed cavity with the wound; a first conduit having a first end adapted to communicate with an interface between said optional layer of porous material and said first layer of flexible wound covering and sealing material and a second end adapted to communicate with vacuum means to establish a negative pressure, in use, between said first covering and sealing material layer and a wound surface; a resiliently compressible wound packing material on top of said first layer of covering and sealing material; a second conduit having a first end adjacent said resiliently compressible wound packing material and a second end adapted to communicate with positive or negative pressure generating means; and a second layer of flexible covering and sealing material over said resiliently compressible wound packing material to form, in use, a second sealed cavity above said first sealed cavity and said wound.

According to a ninth embodiment there is provided a method of providing a dressing including a bag member on a wound on a mammal, the method comprising the steps of: optionally placing a layer of a pressure resistant material which allows fluid transmission therethrough on a bed of the wound; placing an end of a first conduit adjacent said optional layer of pressure resistant material; adhering a first layer of a flexible, wound covering and sealing material on top of the aspirant conduit and layer of pressure resistant material such that said first layer is sealed to skin surrounding the wound and to said first conduit so as to form a first sealed cavity over said wound; placing a resiliently compressible wound packing material in the wound cavity on top of said first sealing layer material; placing an end of a second conduit adjacent said wound packing material; and, placing a second layer of a flexible, adhesive coated wound covering and sealing material over said wound packing material and an area surrounding said wound to seal thereagainst and to said second conduit so as to form a second sealed cavity over said wound.

The layer of pressure resistant material is optional since it may not be needed in the case of small wounds since the vacuum within the first sealed cavity of the dressing may be able to reach substantially all parts of the wound bed without the pressure resistant layer.

It is preferred that the first and second flexible, wound covering and sealing materials are adhesive coated, semi-permeable materials allowing the wound/dressing to breathe. Suitably such materials are thin film materials commonly available and may be made from polyurethanes, such as polyester and polyether polyurethanes, elastomeric polyether polyesters and the like, for example. Common, commercially available materials include OPSITE™ and TEGADERM™, for example. The use of semi-permeable materials is primarily to allow the wound region to breath and prevent maceration of the wound periphery.

In preferred embodiments, the dressing is effectively sealed to the skin surrounding the wound by means of the flexible, adhesive coated film material. However, the term "sealed" is not an absolute requirement nor practically attainable since many flexible dressing membrane materials forming the wound cover are composed of semi-permeable plastics materials which are well known to those skilled in the art. The term semi-permeable is defined as being permeable to water vapour and gases but not liquids and has a transmissibility of moisture vapour greater than 500 g/sq·m/per 24 hr period; if the transmission of moisture vapour is less than this figure then the material is not considered to be semi-permeable. Furthermore, there is almost inevitably some leakage between the skin to which the sealing dressing material is adhered, usually by well known pressure sensitive adhesives, due to hairs and/or other skin surface irregularities and/or imperfections which are not easily completely sealed in absolute terms. Examples of the types of self adhesive, flexible dressing drape materials which are ordinarily used in TNP type therapy as sealing membranes over and around wounds are listed hereinabove and are well known to those skilled in the art and will not be elaborated on further herein unless necessary.

A particular advantage of certain embodiments of bag dressings in comparison with conventional porous type wound packing materials is that the fluids around the wound may be rapidly aspirated away from the wound thus reducing build up of toxins and bacterial burden. Furthermore, pressure in the bag (second sealed cavity) may be changed independently of suction applied to the wound (first) cavity and tissue thus allowing for pain reduction and allowing the application of varying mechanical stress to the tissue.

The layer of pressure resistant material which allows fluid transmission therethrough placed on the wound bed is intended to both support the overlying first flexible layer of sealing material and to prevent it being drawn down into contact with the wound bed when a negative pressure (relative to atmospheric pressure) is applied via the first conduit to the first sealed cavity over the wound. Thus, the purpose of the pressure resistant layer in contact with the wound bed is to resist being crushed by the negative pressure level employed and to permit the establishment of a uniform negative pressure distribution over the whole area of the wound bed and thus render the entire wound area available and susceptible to the benefit of the reduced pressure so as to stimulate blood flow thereto and to some or all of the remaining known benefits of TNP therapy.

A further advantage is that the optional pressure resistant material which contacts the wound may be kept thin and consequently drapeable such that it is able to conform to and remain in contact with the wound surface.

The pressure resistant layer may be porous or may have surface texture or topography such as channels or indentations which allow the transfer of fluids such as aspirant fluid or wound exudate over the area of the layer. The layer of pressure resistant material may be bio-compatible and/or bio-absorbable such as collagen, oxidised cellulose, chitosan, INTEGRA™ or other suitable materials know to those skilled in the art, for example. In such materials it may be advantageous to have pores optimised for promoting the growth of tissue.

It is preferred that the pressure resistant material layer is non-adherent to raw tissue and has small pores sufficiently small to prevent tissue growth into the pores. Such materials are often referred to as "wound contact layers". Whilst the material is referred to as pressure resistant this is only in so far as the material is required to maintain adequate porosity at the desired maximum extent of negative pressure which may be around 250 mmHg below atmospheric pressure.

The pressure resistant material may be bio-absorbable.

The first sealed cavity may also have an optional thin layer of wound packing material on top of the pressure resistant material layer. The layer of wound packing material over the wound may not be required but may be valuable in some large wounds or tunneling or fistula type wounds.

The first conduit may be a flexible plastics material tube having an array of holes therein in the wall thereof in the portion of the conduit which is contained within the dressing first sealed cavity. The first conduit is to apply a negative pressure to the wound first sealed cavity of the dressing thereby both aspirating the wound surface and inter alia stimulating blood flow thereto and also removing wound exudates from the wound site so removing materials which may be detrimental to wound healing. The first conduit may be in operable connection to apparatus having means such as vacuum pump means, for example, for applying a negative pressure.

In some embodiments, optionally one or more additional conduits may also be sealed into operable connection with the first sealed cavity, these conduits being for, for example, the supply of irrigation or cleansing fluids; pharmaceutical agents intended to have healing therapeutic effects on the wound; or to return beneficial fluids which have been removed from the wound site as exudates and mixed with other fluids and treated by, for example, a dialysis technique to the wound. Such techniques are fully discussed in the International patent applications referenced hereinabove.

Thus, the first sealed cavity provided by the first sealing layer of flexible, adhesive coated film material may render some or all of the known beneficial effects of TNP therapy and those additional known techniques mentioned hereinabove in relation to the International patent applications of common ownership herewith to the wound. The first sealed cavity provides in effect an isolated, sealed therapeutic environment for wound healing.

Before carrying out the remaining steps of the method it may be beneficial to employ an optional additional step of applying a negative pressure to the first sealed cavity in order to draw the constituent layers down towards the wound.

The resiliently compressible wound packing material is then placed on top of the first sealing layer such that, preferably, it is just above skin level and is shaped so as to conform generally to the wound shape.

One purpose of the resiliently compressible packing material is to prevent opposite edges of the wound from growing together too quickly and overgrowing the wound itself to form a closed wound cavity.

Preferably, the resiliently compressible packing material may be transparent to enable a clinician, for example, to view the wound to assess healing progress. An example of a suitable material may be a polyurethane based plastics foam material.

The resiliently compressible wound filler may be any suitable porous material such as foam, mesh material, knitted material, corrugated material, for example, and relatively very large pore sizes up to about 10 mm may be employed. Larger pore sizes may be used but there is a limit imposed where the adhesive film may be pulled into the pores by negative pressure effect and may stick to the porous material. However, this latter problem may be overcome by interposing a sheet of a suitable material between the resiliently compressible wound packing material and the second flexible wound covering and sealing material. Suitable materials may include polyethylene and polyvinyl acetate, for example.

The second conduit may be placed adjacent the resiliently compressible wound packing material and the second layer of flexible, adhesive coated sealing material put in place to create the second sealed cavity. The second sealed cavity is isolated from the wound and is present to work or stress the wound tissue for its beneficial effect thereon. The second conduit may be connected to suitable pump means to apply a positive pressure (relative to atmospheric) and/or a negative pressure to the second sealed cavity. In most of the prior art which shows bag members or bladders, they are employed to work or stress the tissue in the wound region by inflation thereof and cycling and/or pulsing, for example, of the pressure within the bladder in a number of different ways. However, none of the bladders shown in the prior art possess the resiliently compressible wound filler illustrated in certain embodiments. Thus the wound being treated by the dressing may be worked or stressed by providing a positive pressure in the second sealed cavity and/or a negative pressure therein. When a negative pressure is applied the effect is that ambient atmospheric pressure serves to compress the resiliently compressible wound filler material which itself, being resilient provides a positive force on the wound bed and surrounding tissue due to its compression and being held against the wound by ambient atmospheric pressure. In the dressing according to a certain embodiment, the ambient atmosphere is not applied to the underside of the second sealed cavity as this space is occupied by the first sealed cavity which itself is sealed from ambient atmospheric pressure on the wound side thus, the stresses acting to expand the wound filler material when compressed act in a downwardly direction against the wound region. The forces provided by the compressed wound filler on the wound may be controlled by, for example, the degree of porosity, pore size, the material from which it is composed and the level of positive or negative pressure applied to the second sealed cavity. Thus, embodiments of the dressing are able to work or stress the wound over a much greater range of conditions. The range of pressures over which the second sealed cavity may be used is from +300 mmHg to −400 mmHg. Typical pressures may lie in the range from about +50 to −200 mmHg, more preferably from +25 mmHg to −150 mm. Inclusion of the compressible filler gives greater range and control particularly for contraction of the wound.

The resiliently compressible wound filling material may be a foam formed in situ in the wound according to patent application, PCT/GB2008/050268, the entire contents of which are incorporated herein by reference.

The fluid used to apply pressure to the second sealed cavity is preferably a gas such as air, for example, but could be a liquid such as water. However, a gas is preferred owing to its compressible nature in case a patient rolls on top of the dressing causing discomfort. The fluid may be pressure pulsed to "work" the tissue surface.

The fluid used to apply pressure may be temperature controlled.

The second layer of flexible, adhesive coated sealing material which finally seals the wound and second cavity may be formed from a stronger film material or a reinforced material so as to resist upwardly directed stresses which put the material under tension, which may cause "ballooning" when the second cavity is inflated with a positive pressure, for example.

Additional conduits may be placed in the first and/or second sealed cavities in order to monitor the pressures therein and/or to supply medication thereto.

A particular advantage of some embodiments of methods of making a dressing is that some or all of the component parts thereof may be tailored to fit the wound under consideration and that no compromises are required thus providing improved wound therapy.

The first and second conduits may be combined into a single, multi-lumen conduit. In this case the first covering and sealing layer may be provided with a port member which accepts the multi-lumen conduit and the fluid flow paths in the multi-lumen conduit being directed as appropriate by the port into the respective first and second sealed cavities.

Such port members may also allow the pressure, negative or positive, in the first and/or second sealed cavities to be monitored and/or controlled by means of additional lumens connected to control/monitoring devices remote from the wound. Such devices may comprise the vacuum/pressure generating means and transducer means, for example, to monitor the pressure at the wound. Such transducer means may be further linked to control means to control the pressure/vacuum generating means and/or valve/air bleed means into the first and/or second sealed cavities.

According to a tenth embodiment there is provided a port member for a dressing, the port member comprising a body portion having flow passages adapted to co-operate with at least two lumens; a face portion adapted to be adhered to a flexible membrane material; and, the flow passages being directed on either side of said face portion.

The port member has at least one fluid flow passage configured to communicate with a region on a first side of the face portion.

The port member has at least one fluid flow passage configured to communicate with a region on a second side of the face portion.

A suitable port member may be molded from a soft plastics material such as polyurethane, silicone or polypropylene, for example, and comprises a base flange face portion having an adhesive layer on at least a peripheral portion of the base flange to allow the port member to be adhered or welded to the first flexible covering and sealing material layer of the dressing. The port member may have at least two fluid flow passages therein adapted to co-operate with first and second conduit lumens. When the port member is adhered to the first flexible covering and sealing material the fluid flow passages in the port member permit fluid flow on each side of the first flexible covering and sealing material film. Thus, one lumen in the conduit is able to apply a negative pressure to the first sealed cavity and the second lumen is able to apply either a negative pressure or a positive pressure to the second sealed cavity as appropriate.

The adhesive layer of the base flange face portion may be protected before use with a known peelable and discardable paper such as siliconised paper for example, prior to adhering the port member to a dressing covering and sealing material.

According to a twelfth embodiment there is provided a kit for the provision of a topical negative pressure therapy dressing for a wound, the kit comprising: pressure resistant porous material for placement, in use, adjacent a wound surface; flexible covering and sealing material adapted, in use, for adhering to sound skin; resiliently compressible porous wound packing material; a conduit comprising at least two lumens; and, a port member having at least two flow passages adapted to co-operate with said two lumens.

BRIEF DESCRIPTION OF THE DRAWINGS

FIGS. 1A and 1B show a part sectioned perspective view of one embodiment of an apparatus embodying a wound filling device.

FIGS. 2A to 2F show various views of embodiments of a sock member and its construction.

FIGS. 3A to 3E shows various sections and views of embodiments of a port member for welding to an inflatable bag member.

FIG. 4A shows an underside plan view of a shroud member; FIG. 4B shows a side view in elevation of the shroud member of FIG. 4A; FIG. 4C shows a top plan view of the shroud member of FIG. 4A; FIG. 4D shows a perspective view of the underside of the shroud member of FIG. 4A; and, FIG. 4E shows a perspective view of the top of the shroud member of FIG. 4A.

FIG. 11 shows a schematic of an embodiment of a plurality of rolled sheets of material being braided together.

FIG. 12 shows a schematic of another embodiment similar to FIG. 11.

FIG. 13 shows a photograph of various embodiments of wound packing members.

FIG. 14 shows a schematic view of an embodiment of a plurality of wound packing units joined together by a linking thread.

DETAILED DESCRIPTION OF THE PREFERRED EMBODIMENT

Figure 4A:
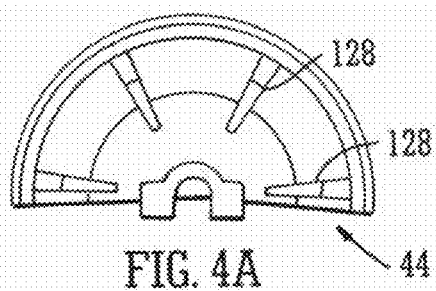
FIGS. 4A to 4E show various sections and views of embodiments of a shroud member to co-operate with the port member of FIG. 3.
Figure 4B:
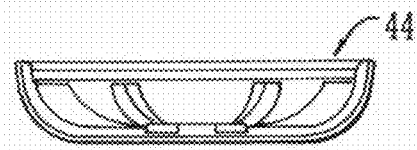
Figure 4C:
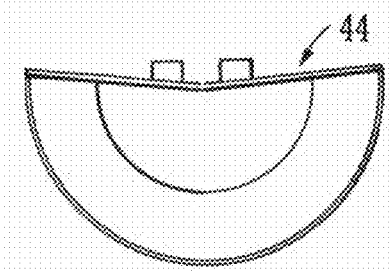
Figure 4D:
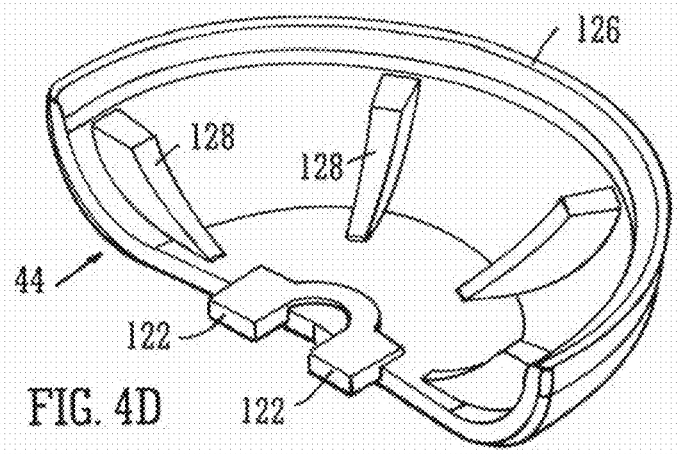
Figure 4E:
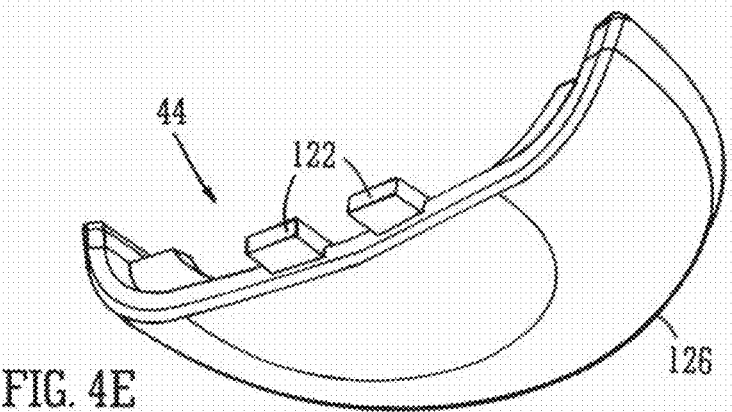
Figure 5:
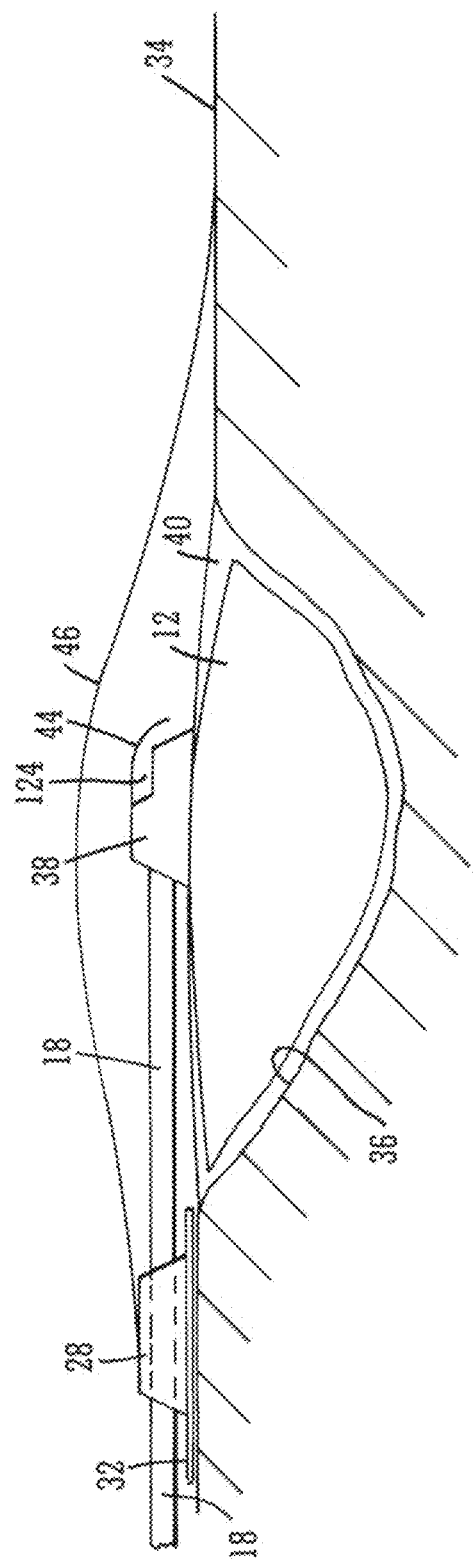
FIG. 5 shows a schematic cross section of an embodiment of a wound having a wound filling device embodied in apparatus for the application of TNP therapy.

Referring now to the drawings and where the same features are denoted by common reference numerals, FIGS. 1A and 1B show a perspective view of one embodiment of a device 10 and FIG. 5 shows a schematic cross section of the device installed in a wound cavity. The device comprises a wound filling inflatable device 12 which may comprise an inflatable bag member 14 and a sock member 16. The inflatable wound filling device 12 is shown in FIG. 1 part sectioned and a detail "A" is shown at a greater magnification in FIG. 1B. The device also comprises a multi-lumen conduit 18 (shown coiled up prior to use) having three separate lumens 20, 22, 24 therethrough. The conduit 18 passes through a hole 26 in a grommet member 28 which itself is adhered by a flange 30 around the periphery of the grommet member 28 to a dressing 32 which is shown in part only and which adheres the grommet 28 to a patients' skin 34 (FIG. 5) adjacent a wound 36 to which TNP therapy is to be applied. The arrangement is shown in a schematic cross section in FIG. 5. At the wound-end of the device the conduit 18 is attached to a port member 38 which has passages therethrough which connect the individual lumens 20, 22, 24: to the interior of the inflatable bag member 14; the wound cavity 40 (see FIG. 5) for the purpose of aspiration thereof; and to the wound cavity 40 for the purpose of providing an air-bleed thereto to maintain a constant negative pressure and/or to monitor pressure in the cavity 40, respectively. A shroud member 44 is provided which clips over the port member 38 for the purpose of preventing an overlying sealing drape membrane 46 from occluding the suction passage in the port member 38 (explained in detail with reference to FIG. 3 below). The drape membrane 46 seals around the periphery of the wound cavity 40 so as to substantially prevent large scale ingress of air as is well known in the TNP art. At the end of the conduit 18 remote from the wound, the conduit has a connector block 50 which connects the lumens 20, 22, 24 to separate conduits 52, 54, 56, respectively which are themselves provided with suitable connectors 60, 62, 64, respectively on their free ends for the purpose of connecting the lumens to a source of air (not shown) to inflate the inflatable bag member 14; to a vacuum source such as a vacuum pump (not shown) to aspirate the wound cavity 40; and, to a pressure relief valve and or pressure transducer (not shown) to provide an air bleed into the wound cavity to maintain a desired negative pressure in the wound cavity 40.

With regard to the dressing 32 and grommet 38 reference is made to GB patent application 0712735.0 and PCT/US 2007/074374 of common ownership herewith, the contents of which are included herein by reference, and which explain in detail the structure and constitution of these features but which are relatively incidental to the present application and could be replaced with any suitable means of sealing the conduit 18 to the sealing drape 46 to prevent ingress of ambient air into the wound cavity from this particular source.

The wound filling device 12 comprises an inflatable bag member 14 having an outer covering sock member 16. The inflatable bag member 14 may be made in certain embodiments by welding two circular sheets 70, 72 of thin, flexible, impermeable plastics material together around their peripheries to form a weld bead 74. The upper sheet 70 has a central circular aperture 76 therein of a size suitable to be affixed to a thin flange 78 around the periphery 80 of the port member 38, the flange 78 and aperture 76 edge being either welded together or adhesively bonded so as to make the inflatable bag member 14 and the port member 38 an integral item.

The sock member 16 may be manufactured from a thin flexible plastics material such as EVA, for example and which has a vacuum-formed textured surface 80. The surface topography comprises an array of hexagonal indentations 82. Some or all of the indentations 82 may have a central perforation 84. The individual hexagons are separated by channels 86 as shown in FIGS. 2C to 2E. FIG. 2F shows the contour of the hexagonal indentations from a side view with upstanding indentations being adjacent the bag surface 16 in use. The sock member may be made from two sheets 90, 92 of the plastics material and which sheets are placed together having the eventual wound contacting surface 94 to the inside as shown in FIG. 2A. The two sheets are welded together around their peripheries to leave a weld bead 96 around the outside, FIGS. 2A and 2B showing the sock member after welding but before turning inside out. The upper sheet 90 has a central aperture 98 therein and after welding together the sock so formed may be turned inside out about the aperture 98 to form the sock as shown in FIG. 2C with weld bead 96 on the inside and the textured surface 94 on the outside. The aperture 98 may be used to insert the inflatable bag member 14 into the sock 16, the aperture 98 fitting around the port member welded flange 78. FIG. 2C shows the sock member 16 with a small portion of the area having the textured surface, however, this for illustration only and the whole upper and lower surface of the sock member 16 may be provided with the textured surface, though not necessarily the same textured surface on both sides. In the illustrated embodiment the hexagons 82 are 2.6 mm across the flats, the central perforations 84 are 0.6 mm in diameter and the depth of the hexagonal indentations from the planar surface is 1.05 mm. However, these dimensions are merely exemplary of one embodiment of a sock member and dimensions may vary according to the needs of a particular wound in other embodiments.

In this embodiment, the sock member may have a textured surface over substantially the whole area thereof, the surface being configured to maintain a continuous flow path for aspirated fluid to the port member 38 as described below.

Although the example of the wound filling device described above is stated to be made with circular sheets of material, it is of course merely exemplary and the inflatable bag 14 and sock member 16 may be made of any suitable shape and size to suit a particular wound shape and size or a range of wound shapes and sizes.

The port member 38 may be moulded from a soft and conformable EVA material, for example, such that if lain upon by a patient no resulting trauma is caused by use of a hard material. The port member 38 comprises a main body portion 100 having passages for connection to lumens 20(52), 22(54), 24(56) in conduit 18 and the flange portion 78 which may be welded to the periphery of aperture 76 of the inflatable bag member around the periphery 80 of the main body portion 100. The port member has a socket portion 102 corresponding to and co-operating with the outer shape of the conduit 18 such that the conduit may be plugged directly into the socket 102 and which effects simultaneous connections with the individual limens 20, 22, 24 therein. Lumen 22 connects with passage 104 which passes through the upper part of the main body portion 100 to communicate with the wound cavity 40 (see FIG. 5) for the purpose of evacuation thereof. Lumen 24 connects with passage 106 for the purpose of providing an air bleed to the wound cavity 40 and/or measuring the actual pressure applied to the wound cavity 40. Passages 104, 106 are connected internally in the port member 38 by virtue of a common connection of lumens 22, 24 in the socket portion 102. Lumen 20 of conduit 18 may be connected individually to passage 108 by means of a raised spigot portion 110 in the base of the socket 102 and which seals with lumen 20 to provide a source of air to the interior of the inflatable bag member 14. Passage 108 communicates with the interior of the inflatable bag member by exiting through the base 112 of the port member as indicated by dashed lines 114 in FIG. 3E. The main body portion 100 may be provided with small blind recesses 120 to receive tongues 122 of a shroud member 44 for the purpose of retaining the shroud member 44 to the port member 38. The shroud member 44 serves to provide an air space or cavity 124 between the port member 38 and the shroud member 44 above and around the exit of passage 104 to the outside of port member 38 so as to prevent it from being occluded by the overlying drape membrane 46 during aspiration (see FIG. 5). The shroud member 44 comprises a half-clam shell body portion 126 sufficiently rigid to withstand the negative pressure applied by the drape membrane 46 without occluding passage 104.

The clam shell body portion 126 may be reinforced against excessive distortion by ribs 128.

The body portion 100 of the port member 38 may have a flanged face portion 78 extending therearound, the lower face of which may be provided with an adhesive layer to enable the port member 38 to be adhered to the sealing drape 46. Before use the adhesive layer may be protected with a siliconised paper layer (not shown) in a known manner. When adhered to the sealing drape 46, the fluid flow passage 106 communicates with the sealing drape 46 through an aperture made in the sealing drape 46 (not shown) and to aspirate fluid inclusive of wound exudate from that cavity and provided a vacuum thereto. The port member described above has three fluid flow passages therethrough, however, the port member may has two passages or even more than three passages and may be tailored to provide other functions in additions to those described.

Figure 6:
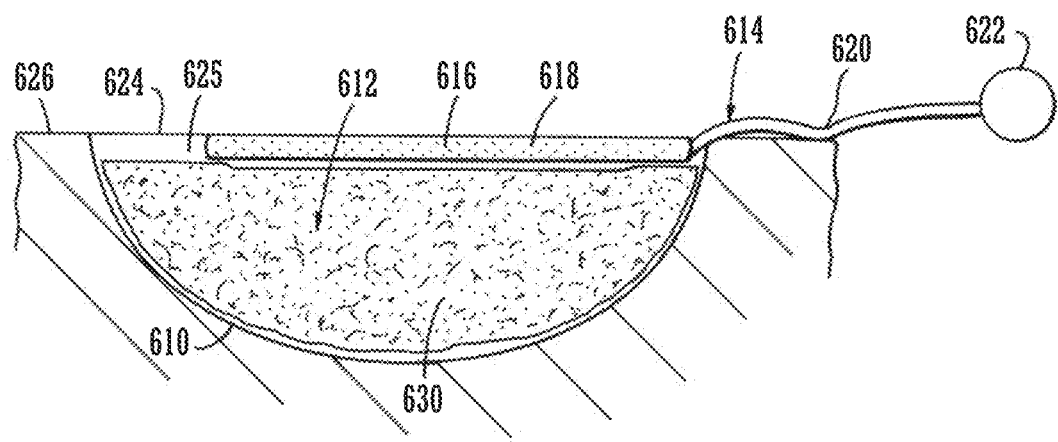
FIG. 6 shows a schematic cross section of a wound having an embodiment of a wound filling device therein as part of a TNP therapy apparatus.

FIG. 6 shows a schematic representation of a wound 610 having a wound filling device 612. The wound filling device 612 has a drain conduit 614 lying on the top thereof, the drain conduit having a portion 616 having a plurality of apertures 618 to aspirate wound exudate within the wound 610 into a second, single lumen portion 620 of the drain conduit which may be operably connected to a vacuum pump 622. A sealing drape 624 overlies the wound 610 to create a sealed wound cavity 625, the sealing drape having a layer of pressure sensitive adhesive (not shown) in known manner on the side which contacts and adheres to sound flesh 626 surrounding the wound 610. The apparatus may also contain in known manner a waste canister (not shown) to receive wound exudate and a power source and control system (both not shown) for the vacuum pump 622.

In this embodiment, the wound filling device 612 comprises a sealed bag member 630 being filed with polystyrene beads of a size range 0.1 to 20 mm preferably 1.0 to 10.0 mm. In some embodiments, the bag material may be embossed (not shown) EVA sheet, cut to size and welded at a seam (not shown) after filling with the beads. In operation and since the bag member 630 is not porous or otherwise permeable, wound exudate may be drawn around the outer surface of the bag member towards the drains conduit portion 616 from whence it is aspirated away from the wound site through the conduit 620 in known manner. Due to the vacuum produced by the pump 622 and the surrounding ambient atmospheric pressure, the wound filling device 612 may be pressed into intimate contact with the wound surface, however, an even vacuum depression may be achieved over the whole wound surface due to the embossed surface texture of the EVA material and the contained polystyrene beads providing a multitude of channels along which exudate may be aspirated. Thus, the interior of the wound filling device 612 and the contained beads do not become filled or saturated with wound exudate and which lessens the bacterial load at the wound 10 thus also lessening the risk of infection.

Figure 7:
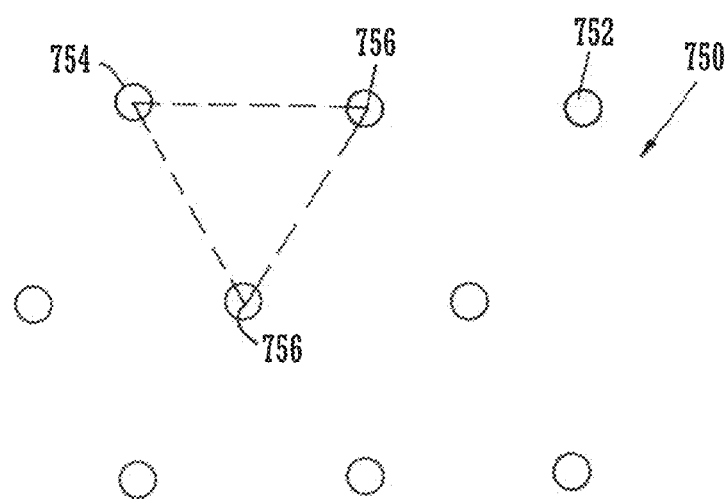
FIG. 7 shows a schematic of an embodiment of a suitable bag member surface.

FIG. 7 shows a schematic of a pattern of surface features suitable to form the surface texture of bag member of a wound filling device. The pattern denoted generally at 750 possesses a multitude of upstanding silicone rubber cylinders 752 (shown in plan view only) of height about 1 mm and diameter 754 of 0.2 mm and having pitched centres 756 1 mm apart and formed in an equilateral triangular array. The silicone rubber material is soft and the cylinders 752 cause no discomfort or trauma to the patient but do provide a multitude of paths for fluid flow.

Figure 8:
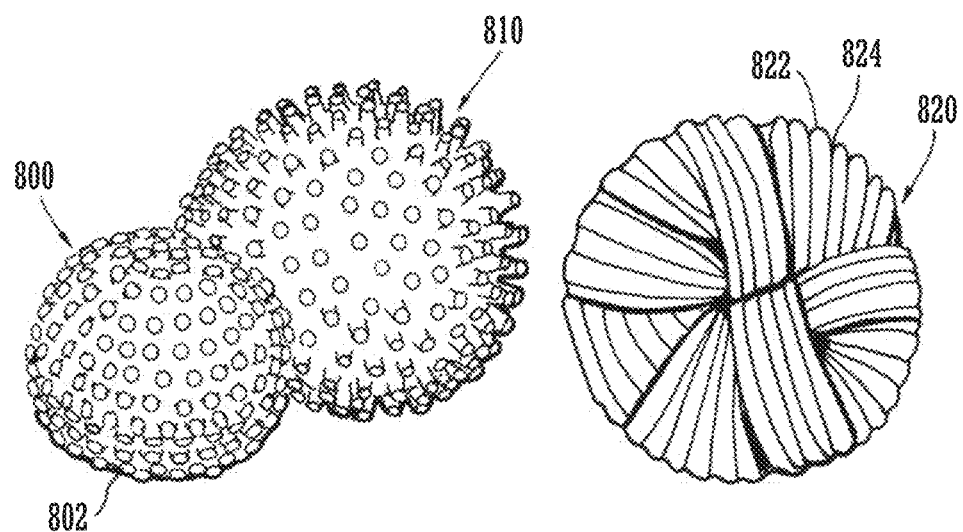
FIG. 8 shows a photograph of embodiments of wound filling devices.

FIG. 8 shows a photograph of three examples of wound filling devices. Device 800 comprises a hollow gas filled moulded ball of polyurethane material having a surface similar to that described with respect to FIG. 7 but with cylindrical protrusions 802 having lower aspect ratio. Device 810 comprises blow moulded polyurethane (Elastane SP806™). Device 820 comprises a moulded polyurethane material ball having a surface provided with ridges 822 and channels 824 in varying orientations.

The wound filling devices in FIG. 8 may also have passages or holes therethrough with the proviso that such passages or holes do not allow exudate to communicate with interior volumes of the ball which may contain gas or beads, for example, of resilient, compressible material.

Figure 9:
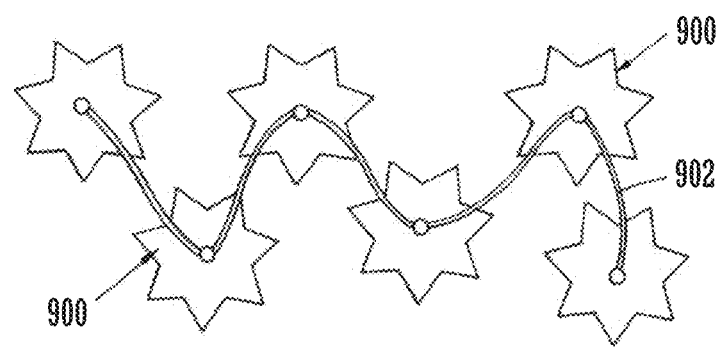
FIG. 9 shows a schematic of a plurality of an embodiment of wound filling devices strung together.

FIG. 9 shows a plurality of schematic wound filling devices 900 strung together by a thread 902. Such a string of devices may be sold as a kit having a plurality of devices thereon, for example twenty, and the clinician may cut off the number which is appropriate to filling the wound.

Figure 10:
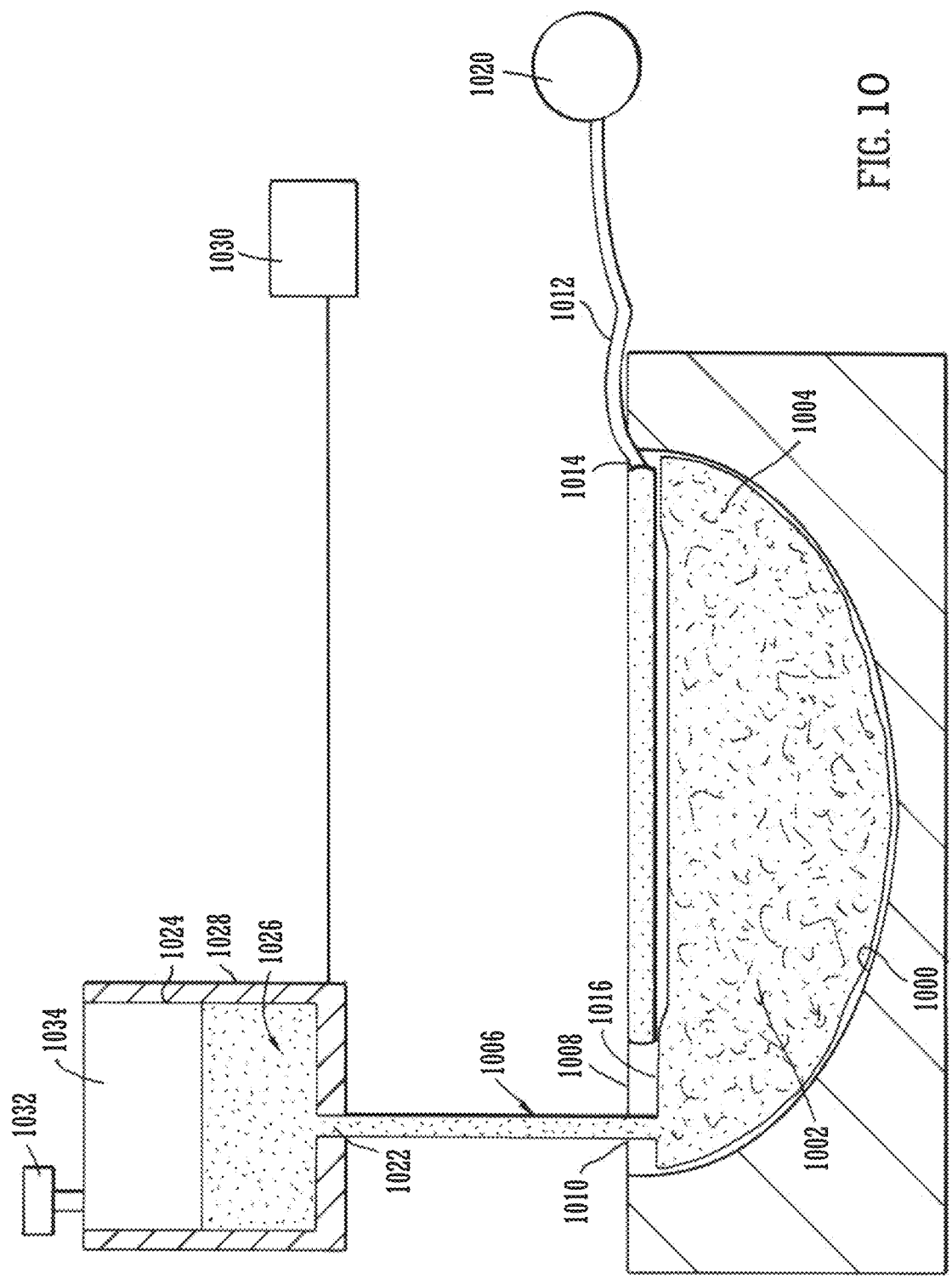
FIG. 10 shows a schematic cross section of a wound having an alternative embodiment of a wound filing device to that shown in FIG. 6.

FIG. 10 shows a schematic alternative embodiment of the wound filling device shown in FIG. 6. A wound 1000 has a wound filling device 1002 therein of a size to fill the wound. The construction of the device 1002 may be similar to the device shown and described with reference to FIG. 6 save for the fact that the bag member 1004 has a flexible conduit 1006 attached thereto to communicate with the interior (not shown) of the bag member 1004 and which conduit passes sealingly through the sealing drape 1008 at the point 1010 thus, no wound exudate is able to enter either the conduit 1006 or the interior of the bag member 1004. An aspirant conduit 1012 passes sealingly through the drape 1008 at point 1014 thus creating a sealed wound cavity 1016 beneath the drape 1008 apart from the connection of the conduit 1012 to a vacuum pump 1020 and any other apparatus features such as a waste canister and associated equipment which may be present in known manner. The conduit 1006 is connected at its distal end 1022 to a reservoir 1024 which contains warm water 1026 which is maintained at a constant temperature by a heating jacket 1028 which has an associated power supply and control system 1030. The reservoir 1024 may be substantially closed to ambient atmosphere but has a 0.2 micron filter 1032 to prevent bacteria from entering an air space 1034 but which permits pressure in the air space 1034 above the water to be maintained at ambient atmospheric pressure. The warm water 1026 fills the bag member 1004 and has valuable therapeutic effects on the wound 1000. The water 1026 in the bag member 1004 may be circulated to an extent by pressure pulsing of the wound cavity 1016. As the vacuum in the wound cavity is increased (i.e. lower pressure relative to ambient) the surrounding ambient atmospheric squeezes the bag member 1004 to expel some of the water back to the reservoir 1024; relaxation of the vacuum allows the bag member to expand thus drawing water at the controlled temperature into the bag member.

Alternatively, in some circumstances it may be beneficial for the fluid 1026 to be cooled rather than heated and the apparatus described above contemplates cooling rather than heating of the fluid 326.

The bag member 1004 may be provided with a stub conduit sealed by a clamp and a separate conduit appropriate to the associated apparatus layout described above attached to the stub by known means.

Further embodiments of wound filling devices may include three-dimensional wound packing members, and certain embodiments may comprise a plurality of such wound packing members linked together. FIG. 11 shows stages in the braiding of three elements designated as 1110, 1112, 1114 into a wound packing member unit. The elements may be formed from a rolled sheet of about A4 size of perforated material such as, for example, perforated polyurethane film such as Elastogran SP806™ of 100 g/m², 0.8 mm perforations at 2 mm pitch centres, having perforations therein, the shape, size and extent of perforations being predetermined so as to arrive at a desired overall porosity and resilience when a plurality of the elements are connected together.

FIG. 12 shows stages in a similar construction to that of FIG. 11 but the four rolled elements comprise Nylon™ net.

FIG. 13 is a photograph showing examples of embodiments of wound packing member units made. Wound packing members denoted at 1350 are plaited structures and those at 1360 are structures rolled like stockings.

FIG. 14 shows a plurality of rolled structures 1400 which are joined together by a common linking monofilament Nylon thread 1402. Although only four wound packing units are shown, a kit comprising a string of say ten units may be provided and the clinician cutting off the appropriate number for the wound size concerned. This provides certainty at wound dressing change time that substantially all of the old wound packing material has been removed from a wound because they are linked together.

Figure 15:
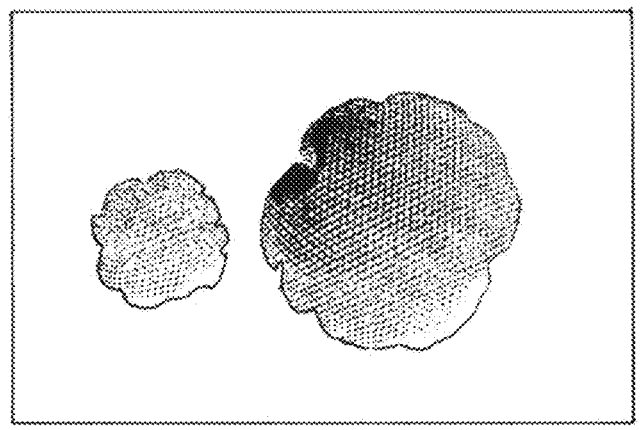
FIG. 15 shows a photograph of two embodiments of wound packing units.

The wound packing unit described above with respect to FIGS. 2A-2E may be used to fill any general wound and FIG. 15 shows two examples of wound packing units; the larger one being approximately 10 cm in diameter and the smaller one approximately 5 cm in diameter.

Figure 16:
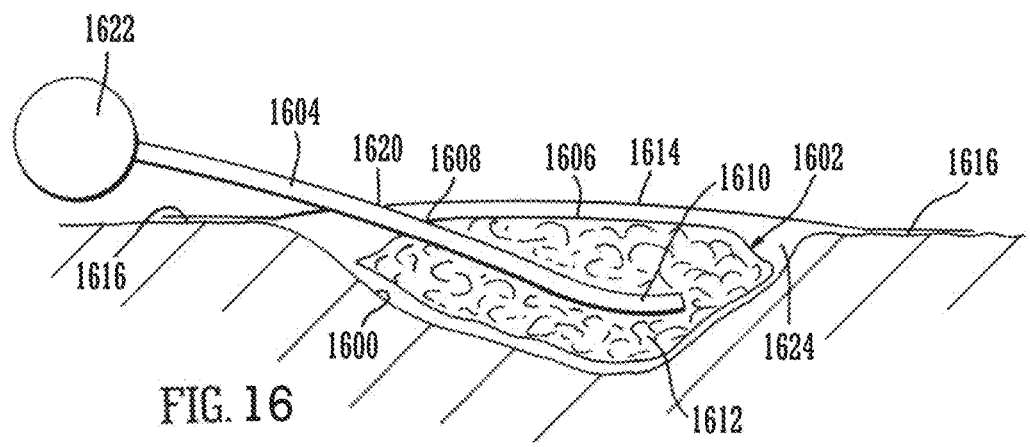
FIG. 16 shows a schematic cross section of one embodiment of a wound packing unit incorporated into a TNP therapy dressing.

FIG. 16 shows a schematic cross section through a wound 1600 being treated with TNP therapy. The wound 1600 has a wound packing unit 1602 as described with reference to FIGS. 2A-2E and is provided as an entity complete with an aspirant conduit 1604 which may be incorporated in and sealed to the bag member 1606 at 1608 where it passes through. The end drain portion 1610 of the conduit 1604 is embedded in and wrapped with the filling material 1612 of the wound packing unit. A sealing drape 1614 may be adhered to the patient's sound flesh 1616 around the border of the wound 1600. The sealing drape 1614 may be provided with a coating of pressure sensitive adhesive (not shown) over the surface which is to be adhered to the patient and the conduit 1604 where it passes through the sealing drape is sealed to the drape by means of the drape being pinched around the conduit itself at 1620. The conduit 1604 may be connected to a vacuum source 1622 such as an electric vacuum pump, for example. The vacuum source may also be associated with a waste receptacle (not shown) in known manner and to which wound exudate from the wound 1600 may be aspirated. The closed volume beneath the sealing drape 1614 forms a wound cavity 1624 which is subject to a negative pressure as created by the vacuum source 1622. Outside ambient atmospheric pressure bears down upon the wound packing unit 1602 so as to compress it and hold the sides/edges of the wound apart to prevent them growing over and forming an occluded cavity in the wound.

Figure 17:
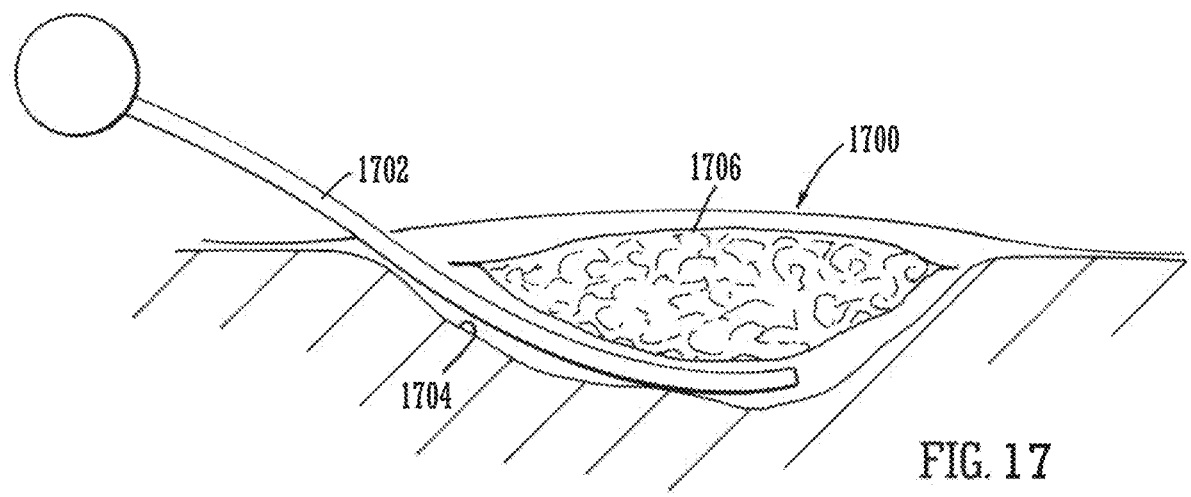
FIG. 17 shows a second embodiment of a wound packing unit incorporated into a TNP therapy dressing.

The embodiment 1700 shown in FIG. 17 may be similar to that of FIG. 16 except that the conduit 1702 may be placed in the wound 1704 separately from the wound packing unit 1706. In essence this embodiment works in a similar manner to that of FIG. 16.

Both the embodiments of FIGS. 16 and 17 work in essentially the same manner in that the vacuum created in the wound cavity is evenly distributed by virtue of the perforations and channels in the embossed material forming the bag member thus, allowing fluid access to and from some or all parts of the wound surface. The perforations and channels allow transport of wound exudate both over the wound surface and also through the interior of the wound packing unit towards the aspirant conduit.

Figure 18:
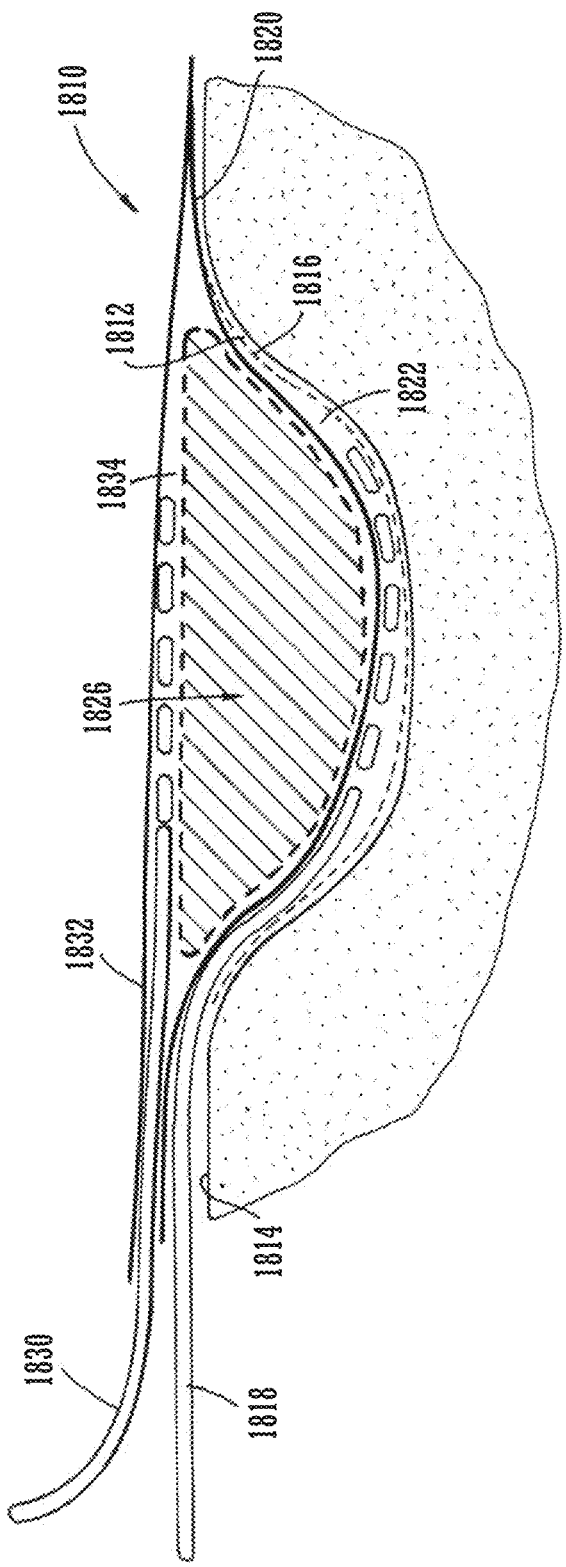
FIG. 18 shows a cross section through a wound having a dressing according to one embodiment.

Referring now to FIG. 18 and where a wound having a dressing is denoted generally at 1810. The wound is denoted at 1812 in the form of a deep depression in the tissue 1814. The dressing may be made by first placing a layer of wound contact material 1816 in direct contact with the wound bed. The wound contact material 1816 may be a porous, pressure resistant material which resists crushing at negative pressures of a maximum of about −250 mmHg below atmospheric and serves to maintain a uniform pressure distribution over the area of the wound. Suitable materials may include Gazetex™ gauze bandage roll supplied by Derma Sciences Inc., CAVICARE™ supplied by Smith & Nephew, open cell reticulated polyurethane foam, Mepitel™ supplied by Molnlycke, for example. A first conduit 1818 may be laid in the wound on top of the wound contact layer, the conduit being a soft flexible plastics material able to conform to the wound shape. A first flexible, adhesive coated film drape material 1820 may be then laid over the whole area of the wound and over a surrounding area of sound tissue to adhere thereto and thus to create a first sealed cavity 1822 adjacent the wound 1812, the first conduit 1818 being sealed to the first cavity by pinching the drape material 1820 thereround in known manner (not shown). A piece of resiliently compressible foam wound packing material 1826 may be placed in the wound 1812 on top of the drape material 1820, the packing material being shaped to the wound and standing slightly proud of the surrounding sound tissue 1814. The first sealed cavity 1822 may have a negative pressure applied thereto via the conduit 1818 to draw the first drape material 1820 down onto the wound contact material 1816 so that the wound shape may be more accurately ascertained prior to preparation and placing of the wound packing material 1826. A second conduit 1830 may be then placed on or in the wound packing material 1826, the conduit 1830 being operably connected to means for providing a positive and/or negative pressure in the final dressing. Lastly a second layer of flexible, adhesive coated film drape material 1832 may be laid over the entire wound and surrounding sound tissue to bond, preferably with the border of the first layer of sealing material 1820 or, to sound tissue, the second drape material being pinched around the conduit 1830 to seal therewith (not shown) and to form a second sealed cavity 1834.

Figure 19:
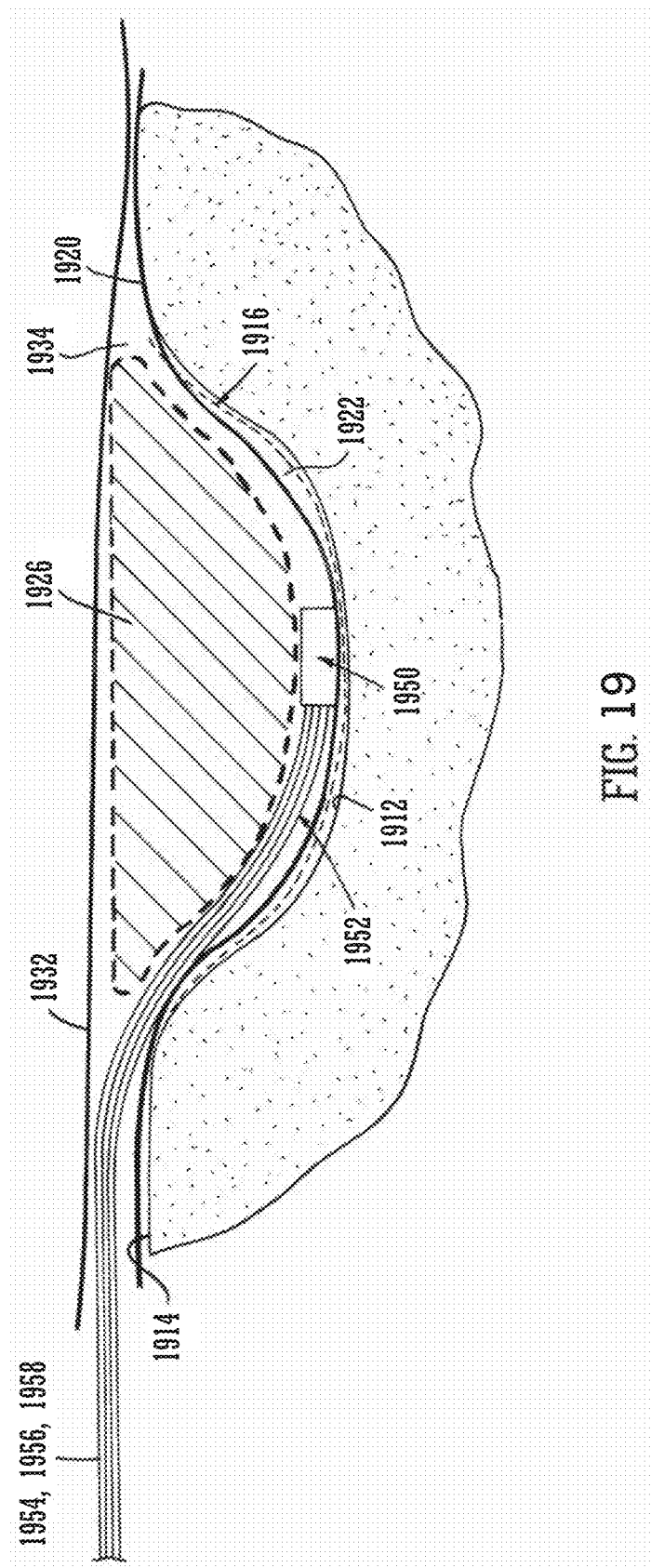
FIG. 19 shows a cross section through a wound having a dressing according to another embodiment.

Referring now to FIG. 19, FIG. 19 illustrates an embodiment of a similar cross section to that of FIG. 18 wherein the wound dressing may be operably associated with a port member, for example the port illustrated in FIGS. 3A-3E. This embodiment comprises: a wound contacting layer 1916 of a pressure resistant porous material; a first flexible covering and sealing film material 1920; a wound packing material 1926; and, a second flexible covering and sealing material 1932; together with a first sealed cavity 1922 and a second sealed cavity 1934. Thus, many of the basic features of this second embodiment are essentially the same as the first embodiment. However, this second embodiment comprises a port member 1950 adhered to the first covering and sealing layer 1920. This embodiment is compatible with a variety of port members, including the port illustrated in FIGS. 3A-3E, described above. The port member 1950 may be adapted to receive a multi-lumen conduit 1952 which in this case has three lumens therethrough. Two lumens communicate with the first sealed cavity 1922 and the third lumen communicates with the second sealed cavity 1934. The distal ends of the lumens are in co-operating and operable communication with: vacuum means (not shown)

to aspirate the first sealed cavity 1922 and to maintain a predetermined vacuum therein; transducer means to monitor and control the pressure within the first sealed cavity; and, pressure/vacuum generating means to apply pressure or vacuum as appropriate to the second sealed cavity, respectively. Thus, the port member 1950 maintains the first and second sealed cavities independent and sealed from each other.

As will be seen from the above two embodiments, it is possible to provide a dressing to both aspirate a wound by TNP therapy giving some or all of the benefits associated therewith by the first sealed cavity and also simultaneously to work or stress a wound to provide benefits associated with that therapeutic technique in one dressing by pressure pulsing or cycling through positive and negative pressures by the second sealed cavity.

As will be appreciated from the above, complex dressings can be made from component parts held in most hospitals.

Further embodiments can be seen in the following paragraphs:

1. A wound filling device for use in apparatus for the application of topical negative pressure therapy to a site on the body of a mammal, the device comprising: an inflatable bag member having at least one fluid carrying conduit operably connected thereto to inflate/deflate said bag member; a separate textured covering sock member at least partially covering the inflatable bag member.
2. A wound filling device according to paragraph 1 wherein the bag member is made from two sheets of material welded together at their outer peripheries.
3. A wound filling device according to either paragraph 1 or paragraph 2 wherein the sock member is made from two sheets of material welded together at their outer peripheries.
4. A wound filling device according to paragraph 3 wherein the sock member has said weld contained within the interior of the sock.
5. A wound filling device according to paragraph 1 wherein the sock member is moulded.
6. A wound filling device according to any one preceding paragraph wherein the sock member has an aperture therein for the insertion of the bag member thereinto.
7. A wound filling device according to any one preceding paragraph wherein the bag member and the sock member are able to slide relative to each other during inflation or deflation of the bag member.
8. A wound filling device according to any one preceding paragraph wherein the sock member is made from thin textured sheet plastics material.
9. A wound filling device according to any one preceding paragraph wherein the texturing comprises a 3-dimensional pattern.
10. A wound filling device according to paragraph 8 wherein the 3-dimensional pattern provides aspiration channels for drainage of wound exudate between an outer surface of the bag member and an inner surface of the sock member.
11. A wound filling device according to paragraph 9 wherein the 3-dimensional pattern also provides aspiration channels for wound exudate between an outer surface of the sock member and the wound surface.
12. A wound filling device according to any one of paragraphs 7 to 10 wherein the texturing comprises an array of repeated indentations.
13. A wound filling device according to paragraph 11 wherein at least some the indentations have a perforation therein.
14. A wound filling device according to any one of paragraphs 7 to 13 wherein the texturing comprise an array of repeated octagonal shapes.
15. A wound filling device according to any one preceding paragraph wherein the bag member is provided with a conduit port member attached thereto for the attachment of said at least one fluid carrying conduit.
16. A wound filling device according to paragraph 15 wherein the port member also provides passages therein for the connection of a wound cavity aspiration conduit.
17. A wound filling device according to paragraph 15 or 16 wherein the port member has a passage therein to co-operate with a further conduit to provide an air bleed and/or pressure reference connection.
18. A wound filling device according to any one of paragraphs 15 to 17 wherein the port member has a shroud member to prevent, in use, occlusion of an aspiration port therein by an overlying wound sealing membrane.
19. A wound filling device substantially as hereinbefore described with reference to the accompanying description and drawings.
20. Apparatus for the application of topical negative pressure therapy to a wound on the body of a mammal, the apparatus comprising: a wound filling device according to any one of preceding paragraphs 1 to 19; an aspiration conduit connected to aspiration means; and a sealing membrane for sealing said wound and defining a wound cavity.
21. Apparatus according to paragraph 20 further comprising an additional conduit to said wound cavity.
22. Apparatus according to paragraph 21 wherein said additional conduit is a bleed or reference pressure conduit.
23. Apparatus for the application of topical negative pressure therapy to a wound on the body of a mammal substantially as hereinbefore described with reference to the accompanying description and drawings.
24. A dressing for the application of topical negative and/or positive pressure therapy to a wound, the dressing comprising in use: an optional layer of a pressure resistant porous material adjacent a surface of a wound to be treated; a first layer of a flexible wound covering and sealing material on top of the optional pressure resistant porous material adapted, in use, to surround the wound and seal against sound tissue to form, in use, a first sealed cavity with the wound; a first conduit having a first end adapted to communicate with an interface between said optional layer of porous material and said first layer of flexible wound covering and sealing material and a second end adapted to communicate with vacuum means to establish a negative pressure, in use, between said first covering and sealing material layer and a wound surface; a resiliently compressible wound packing material on top of said first layer of covering and sealing material; a second conduit having a first end adjacent said resiliently compressible wound packing material and a second end adapted to communicate with positive or negative pressure generating means; and a second layer of flexible covering and sealing material over said resiliently compressible wound packing to form, in use, a second sealed cavity above said first sealed cavity and said wound.

25. A dressing according to paragraph 24 wherein the resiliently compressible wound packing material is transparent.
26. A dressing according to paragraph 24 wherein the resiliently compressible wound packing material is made from a polyurethane material.
27. A dressing according to any one of preceding paragraphs 24 to 26 wherein the first layer of flexible covering and sealing material is provided with a port member.
28. A dressing according to paragraph 27 wherein the port member receives said first and second conduits.
29. A dressing according to paragraph 28 wherein the first and second conduits are in the form of a single multi-lumen conduit.
30. A dressing according to any one of preceding paragraphs 27 to 29 wherein said port member directs fluid flow in said conduits with respect to said first sealed cavity and said second sealed cavity as appropriate.
31. A dressing according to any one of preceding paragraphs 27 to 30 wherein said port member is adapted to receive three lumens.
32. A dressing according to paragraph 31 wherein a third lumen is adapted to be operably connected to transducer means to monitor, in use, pressure in said first sealed cavity.
33. A dressing according to any one of preceding paragraphs 27 to 32 wherein said port member is bonded to said first layer of flexible covering and sealing material.
34. A dressing according to any one preceding paragraphs 27 to 33 wherein the port member maintains the first and second sealed cavities independent of each other with respect to pressure.
35. A port member for a dressing, the port member comprising a body portion having flow passages adapted to cooperate with at least two lumens; a face portion adapted to be bonded to a flexible membrane material; and, the flow passages being directed on either side of said face portion.
36. A port member according to paragraph 35 adapted to receive a conduit in the form of a single multi-lumen conduit.
37. A port member according to either paragraph 35 or paragraph 36 having at least one fluid flow passage configured to communicate with a region on a first side of said face portion.
38. A port member according to any one of preceding paragraphs 35 to 37 and having at least one fluid flow passage configured to communicate with a region on a second side of said face portion.
39. A kit for the provision of a topical negative pressure therapy dressing for a wound, the kit comprising: pressure resistant porous material for placement, in use, adjacent a wound surface; flexible covering and sealing material adapted, in use, for adhering to sound skin; resiliently compressible porous wound packing material; a conduit comprising at least two lumens; and, a port member having at least two flow passages adapted to co-operate with said two lumens
40. A method of providing a dressing including a bag member on a wound on a mammal, the method comprising the steps of: optionally placing a layer of pressure resistant material which allows for transmission of fluid on a bed of the wound; placing an end of a first conduit adjacent said optional pressure resistant material; adhering a first layer of a flexible, wound covering and sealing material over the aspirant conduit and pressure resistant material such that said first layer of flexible material is sealed to skin surrounding the wound and to said first conduit so as to form a first sealed cavity over said wound; placing a resiliently compressible wound packing material in the wound cavity on top of said first sealing layer material; placing an end of a second conduit adjacent said wound packing material; and adhering a second layer of a flexible, wound covering and sealing material over said wound packing material and an area surrounding said wound to seal thereagainst and to said second conduit so as to form a second sealed cavity over said wound.
41. A method according to paragraph 40 wherein said first and second flexible, wound covering and sealing materials are semi-permeable materials.
42. A method according to either paragraph 40 or paragraph 41 wherein the first and second flexible, wound covering and sealing materials are coated with an adhesive.
43. A method according to any one of preceding paragraphs 40 to 42 wherein an optional layer of wound packing material is placed on top of the optional layer of pressure resistant wound contact material.
44. A method according to any one of preceding paragraphs 40 to 43 wherein the optional layer of pressure resistant material has a surface selected from the group comprising; porous, textured or channeled.
45. A method according to any one of preceding paragraphs 40 to 44 wherein the optional layer of pressure resistant material is bio-absorbable.
46. A method according to any one of preceding paragraphs 40 to 45 further including the step of applying a negative pressure to the first sealed cavity prior to creating the second sealed cavity.
47. A method according to any one of preceding paragraphs 40 to 46 further including the step of including one or more additional conduits in at least one of the first and second sealed cavities.
48. A method according to any one of preceding paragraphs 40 to 47 wherein the second sealed cavity is subjected to a pressure range from positive pressures to negative pressures.
49. A method according to any one of preceding paragraphs 40 to 48 wherein a fluid is used to apply pressure to said wound by inflating the second cavity.
50. A method according to paragraph 49 wherein the fluid is temperature controlled.
51. A method according to either paragraph 48 or paragraph 49 wherein the applied pressure is pulsed.
52. A method according to any one of preceding paragraphs 40 to 51 wherein the resiliently compressible wound packing material is a foam created in-situ.
53. A method of making a three-dimensional wound packing member, the method comprising the steps of: taking material selected from the group consisting of perforated sheet, net, woven, non-woven and knitted material; subjecting the at least one material to at least one forming process selected from the group consisting of rolling into tubes, braiding, plaiting, knotting and knitting, so as to form a three-dimensional and resilient structural wound packing unit member for packing into a wound characterised by a porosity level of the wound packing unit member being controlled by a degree of tightness of said forming process.
54. A method according to paragraph 53 wherein rolled tubes of the selected material are then formed into a resilient wound packing unit member by a forming process selected from the group consisting of braiding, plaiting, knotting and knitting, so as to form a resilient structural wound packing unit member.

55. A method according to paragraph 53 or paragraph 54 wherein the individual wound packing member units are further treated by a technique selected from the group consisting of adhesively bonding, heat sealing and mechanically fixing to preserve a structural integrity of each wound packing unit member.

56. A method according to any one of paragraphs 53 to 55 further comprising the step of linking together a plurality of the individual structural wound packing unit members so formed into a chain.

57. A method according to paragraph 56 further comprising the step of cutting the chain into an appropriate number of units to suit a specific wound to be treated.

58. A method according to paragraph 56 or paragraph 57 wherein the wound packing member units are linked by a thread.

59. A method according to paragraph 58 wherein the thread is a plastics material monofilament.

60. A method according to any of paragraphs 53 through 59 wherein when the selected material is rolled into a tube, the porosity of the tube is partly controlled by the degree of tightness of rolling.

61. A method according to paragraph 58 wherein a porosity of the resulting wound packing member unit is partly controlled by the degree of tightness of a plaiting, braiding, knitting or knotting step.

62. A method according to any of paragraphs 53 through 61 wherein materials comprising said wound packing member units do not adhere to growing tissue.

63. A method of making a three-dimensional wound packing member according to paragraph 53 wherein a tube is first formed by rolling of the selected material and them forming said tube into a doughnut shape by rolling of the tube along its axis.

64. A three-dimensional wound packing member unit comprising a material selected from the group consisting of perforated sheet, net, woven, non-woven and knitted material, wherein the material is processed so as to form a three-dimensional and resilient structural wound packing unit member, and wherein the wound packing member has a porosity level controlled by the processing.

65. A three-dimensional wound packing member unit when made according to any one of the methods in paragraphs 53 to 64.

66. A kit comprising a plurality of three-dimensional wound packing member units according to paragraph 64.

67. A method of making a three-dimensional wound packing member substantially as hereinbefore described with reference to the accompanying description and FIG. 11; or FIG. 12; or FIG. 13 of the drawings.

68. A three dimensional wound packing member unit substantially as hereinbefore described with reference to the accompanying description and FIG. 11; or FIG. 12; or FIG. 13 of the drawings.

69. A kit comprising a plurality of three-dimensional wound packing member units substantially as hereinbefore described with reference to the accompanying description and FIG. 11; or FIG. 12; or FIG. 13; or FIG. 14 of the drawings.

70. A wound packing unit comprising a resilient, fluid absorbent material contained within a porous bag member, the porous bag member being made of a material which is non-adherent to the wound and characterised in that the porous bag member is formed from a laminated material.

71. A wound packing unit according to paragraph 70 wherein the resilient, fluid absorbent material is selected from the group consisting of gauze, foams, and non woven materials.

72. A wound packing unit according to either paragraph 70 or paragraph 71 wherein the porous bag member material is a sheet or net material 73. A wound packing unit according to any one of preceding paragraphs 70 to 72 wherein the material from which an outer surface of the porous bag member is formed is selected from the group consisting of EVA, PU, PP, PE, silicone, carbomethoxy cellulose and polyacrylate.

74. A wound packing unit according to paragraph 72 wherein the sheet material is selected from the group consisting of perforated and embossed sheet, woven materials, non-woven fibrous sheet, foams, and electrospun nano fibres.

75. A wound packing unit according to paragraph 74 wherein the sheet material is coated in gel.

76. A wound packing unit according to paragraph 74 wherein the sheet material is coated in silver.

77. A wound packing unit according any one of preceding paragraphs 70 to 76 wherein the resilient, fluid absorbent material is treated with silver.

78. A wound packing unit according to any one of preceding paragraphs 70 to 0 wherein the resilient, fluid absorbent material is treated with biologically active components.

79. A wound packing unit according any one of preceding paragraphs 70 to 78 further having combined therewith a conduit for use in topical negative pressure therapy.

80. A wound packing unit according to any one of preceding paragraphs 70 to 79 wherein the bag member comprises two sheets of material joined at their peripheries to form a pocket therein to receive the resilient, fluid absorbing material therein.

81. A wound packing member according to according to any one of preceding paragraphs 70 to 80 wherein the laminated material comprises a foam material between two outer layers.

82. A wound packing unit according to paragraph 81 wherein the laminated material comprises a predetermined pattern of cells or pockets.

83. A wound packing unit according to paragraph 82 wherein the cells or pockets are formed by welding together of the two outer layers.

84. A wound packing unit according to paragraph 82 or paragraph 83 wherein the bag material has a quilted texture.

85. A wound packing unit according to any one of preceding paragraphs 82 to 84 where some cells are unperforated.

86. A wound packing unit substantially as hereinbefore described with reference to the accompanying description and FIGS. 2A to 2E; or FIG. 15; or FIG. 16; or FIG. 17 of the drawings.

87. A method for packing a wound cavity comprising the steps of; forming a wound packing unit by enclosing a resilient absorbent material within a porous bag member, the porous bag member being made of a material which is non-adherent to the wound and characterised in that the porous bag member is formed from a laminated material.
88. A method according to paragraph 87 wherein the wound cavity is treated by topical negative pressure therapy.
89. A method for packing a wound cavity substantially as hereinbefore described with reference to the accompanying description and FIGS. 2A to 2E; or FIG. 15; or FIG. 16; or FIG. 17 of the drawings.
90. A wound filling device comprising a non-porous bag member, the bag member being sealed against ingress of wound exudate and being filled with resilient, compressible material characterised in that an interior of the bag member is provided with means to connect a fluid supply thereto.
91. A wound filling device according to paragraph 90 wherein the bag member is provided with a surface texture.
92. A wound filling device according to paragraph 91 wherein the surface texture permits a uniform pressure distribution to be achieved, in use, in a wound.
93. A wound filling device according to either paragraph 91 or paragraph 92 wherein the surface texture permits uniform fluid flow over an area of a wound.
94. A wound filling device according to any of paragraphs 91 to 93 wherein the surface texture is selected from the group consisting of cylindrical-shaped protrusions, pimples, channels, pathways and ribs.
95. A wound filling device according to paragraph 94 wherein fluid channels and pathways on the surface of the bag member are about 0.5 to 2.0 mm deep.
96. A wound filling device according to any of paragraphs 90 through 95 wherein the bag member is made from a material selected from the group consisting of HDPE, PU, silicone, and EVA.
97. A wound filling device according to any of paragraphs 90 through 96 wherein the resilient, compressible filling of the bag member comprises foam or polystyrene beads.
98. A wound filling device according to any of paragraphs 90 through 97 wherein the filing of the bag member has a material hardness in the region of 70 Shore.
99. A wound filling device according to any of paragraphs 90 through 98 wherein the fluid supplied to the interior of the bag member is a heated fluid.
100. A wound filling device according to any of paragraphs 90 through 98 wherein the fluid supplied to the interior of the bag member is a cooled fluid.
101. A wound filling device according to either paragraph 99 or paragraph 100 wherein the supplied fluid is a liquid.
102. A wound filling device according to any of paragraphs 90 through 96 wherein the resilient, compressible filling is a gas.
103. A wound filling device according to any of paragraphs 90 through 102 wherein the outer surface of the bag member is treated with a biologically active component.
104. A wound filling device according to according to any of paragraphs 90 through 103 wherein the bag member is treated with a chemical non-adherent to tissue.
105. A wound filling device according to any of paragraphs 90 through 104, wherein the wound filling device comprises at least one additional wound filling device attached thereto.
106. A wound filling device according to paragraph 105 wherein the wound filling device is attached to the at least one additional wound filling device with a thread.
107. A wound filling device according to paragraph 106 wherein the thread is a polymer monofilament.
108. A wound filling device according substantially as hereinbefore described with reference to the accompanying description and FIG. 6; or FIG. 7; or FIG. 8; or FIG. 9; or FIG. 10 of the drawings.
109. A kit comprising a plurality of wound filling devices strung together.
110. A kit comprising a plurality of wound filling devices substantially as hereinbefore described with reference to the accompanying description and FIG. 9 of the drawings.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. It will be clear to a person skilled in the art that features described in relation to any of the embodiments described above can be applicable interchangeably between the different embodiments. All possible combinations and subcombinations are intended to fall within the scope of this disclosure. Many of the embodiments described above include similar components, and as such, these similar components can be interchanged in different embodiments.

For example the unitary conduit 18 may be changed for separate conduits and an appropriate grommet member 28 or the grommet may be dispensed with and the conduits sealed to the overlying drape as is known in the TNP art. Similarly, the port member may be adapted to co-operate with separate conduits and a shroud member appropriately modified so as to be able to aspirate the wound cavity without hindrance. The form of the texturing of the sock surface and the material of which it is made may be varied insofar as the sock does not cause unnecessary trauma to the wound and is able to maintain an even pressure distribution over the whole of the wound surface area. These and many other modifications may be made without departing from the scope or spirit of the present application.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example are to be understood to be applicable to any other aspect, embodiment or example described herein unless incompatible therewith.

What is claimed is:

1. A wound treatment device, comprising:
a wound contacting member for treating a wound, the wound contacting member comprising a plurality of shapes and a plurality of ribs, individual ribs of the plurality of ribs having a first end coupled to a respective shape of the plurality of shapes and a second end coupled to another rib of the plurality of ribs.

2. The wound treatment device of claim 1, wherein individual shapes of the plurality of shapes are polyhedral.

3. The wound treatment device of claim 2, wherein individual shapes comprise six or more faces.

4. The wound treatment device of claim 1, wherein individual shapes of the plurality of shapes are circular.

5. The wound treatment device of claim 1, wherein the wound contacting member is configured to be rolled and placed at least partially into the wound.

6. The wound treatment device of claim 1, wherein the wound contacting member is configured to be knotted and placed at least partially into the wound.

7. The wound treatment device of claim 1, wherein the shapes are uniform.

8. The wound treatment device of claim 1, wherein individual ribs are coupled to two other ribs of the plurality of ribs.

9. The wound treatment device of claim 1, further comprising a porous layer.

10. The wound treatment device of claim 9, wherein the porous layer comprises foam.

11. The wound treatment device of claim 1, wherein the wound contacting member comprises a plurality of openings.

12. The wound treatment device of claim 1, wherein the wound contacting member is configured to be connected to a source of negative pressure.

13. The wound treatment device of claim 1, wherein the wound contacting member is configured to apply micro-stresses to a wound.

14. A method of treating a wound, the method comprising:
positioning a wound contacting member at least partially within a wound, the wound contacting member comprising a plurality of shapes and a plurality of ribs, individual ribs of the plurality of ribs having a first end coupled to a respective shape of the plurality of shapes and a second end coupled to another rib of the plurality of ribs; and
applying negative pressure to the wound.

15. The method of claim 14, wherein individual shapes of the plurality of shapes are polyhedral.

16. The method of claim 14, wherein individual shapes of the plurality of shapes are circular.

17. The method of claim 14, wherein the wound contacting member comprises a plurality of openings.

18. The method of claim 14, wherein individual ribs are coupled to two other ribs of the plurality of ribs.

19. The method of claim 14, wherein the wound contacting member is configured to apply micro-stresses to the wound.

20. The method of claim 14, wherein the wound contacting member comprises a porous layer.

* * * * *